US012751751B2

(12) United States Patent
Navarro Vale et al.

(10) Patent No.: US 12,751,751 B2
(45) Date of Patent: Oct. 6, 2026

(54) TEMPORARY ANTIMICROBIAL CEMENT SPACER, ASSEMBLY, KIT, AND METHOD OF MANUFACTURE

(71) Applicant: DePuy Synthes Products, Inc., Raynham, MA (US)

(72) Inventors: Geoffrey Navarro Vale, Fall River, MA (US); Charles Florek, Downingtown, PA (US); David A. Armbruster, West Chester, PA (US); Stanley J. Kmiec, Jr., Morgantown, PA (US); Eric M. Cozzone, Glenmoore, PA (US); Junior Julien, West Chester, PA (US); Michael Good, West Chester, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 5 days.

(21) Appl. No.: 18/971,528

(22) Filed: Dec. 6, 2024

(65) Prior Publication Data

US 2025/0099149 A1 Mar. 27, 2025

Related U.S. Application Data

(62) Division of application No. 17/466,479, filed on Sep. 3, 2021, now Pat. No. 12,186,000.

(Continued)

(51) Int. Cl.

*A61B 17/88* (2006.01)
*A61B 17/00* (2006.01)

(52) U.S. Cl.

CPC ...... *A61B 17/8811* (2013.01); *A61B 17/8816* (2013.01); *A61B 17/8819* (2013.01); *A61B 17/8822* (2013.01); *A61B 2017/00889* (2013.01)

(58) Field of Classification Search

CPC ... A61B 17/8811; A61B 17/74; A61B 17/742; A61B 17/744

See application file for complete search history.

(56) References Cited

U.S. PATENT DOCUMENTS 2,627,768 A 2/1953 Cook
2,683,308 A 7/1954 Cook (Continued)

FOREIGN PATENT DOCUMENTS

CN 201085665 Y 7/2008
CN 103857362 A 6/2014

(Continued)

OTHER PUBLICATIONS

Coilhose Pneumatics, Tubing Cutters product page, http://coilhose.com/index.php/plastic-tubing/tubing-cutters.html, webpage accessed on Oct. 14, 2021.

*Primary Examiner* — Anu Ramana
(74) *Attorney, Agent, or Firm* — Condo Roccia Koptiw LLP

(57) ABSTRACT

The present disclosure is directed to temporary antimicrobial-eluting cement spacer implants, and assemblies, kits, and methods for forming the same. Particularly preferred disclosures are to modular spacers, assemblies, and kits, as well as methods of manufacturing the same, where the modular nature of the spacer permits the selection of specific desired length spacers, as well as specific selection of antimicrobial compounds and dosages, along with the components and processes for forming the same.

16 Claims, 25 Drawing Sheets

Related U.S. Application Data

(60) Provisional application No. 63/074,516, filed on Sep. 4, 2020.

(56) References Cited

U.S. PATENT DOCUMENTS

| | | | | |
|---|---|---|---|---|
| 3,151,510 | A | 10/1964 | Bunker et al. | |
| 4,873,969 | A | 10/1989 | Huebsch | |
| 4,905,373 | A | 3/1990 | Krampe | |
| 4,947,549 | A | 8/1990 | Genovese et al. | |
| 5,050,302 | A | 9/1991 | Mills | |
| 5,064,426 | A | 11/1991 | Huebsch | |
| 5,133,771 | A | 7/1992 | Duncan et al. | |
| 5,171,282 | A | 12/1992 | Pequignot | |
| 5,190,544 | A | 3/1993 | Chapman et al. | |
| 5,336,700 | A | 8/1994 | Murray | |
| 5,337,479 | A | 8/1994 | Ducret | |
| 5,433,718 | A | 7/1995 | Brinker | |
| 5,501,687 | A | 3/1996 | Willert et al. | |
| 5,618,286 | A | 4/1997 | Brinker | |
| 5,897,592 | A | 4/1999 | Caldarise et al. | |
| 5,980,573 | A | 11/1999 | Shaffner | |
| 6,138,362 | A | 10/2000 | Yoshimori | |
| 6,155,812 | A | 12/2000 | Smith et al. | |
| 6,168,595 | B1 | 1/2001 | Durham et al. | |
| 6,193,761 | B1 | 2/2001 | Treacy | |
| 6,245,111 | B1 | 6/2001 | Shaffner | |
| 6,296,667 | B1 | 10/2001 | Johnson et al. | |
| 6,361,731 | B1 | 3/2002 | Smith et al. | |
| 6,443,988 | B2 | 9/2002 | Felt et al. | |
| 6,530,956 | B1 | 3/2003 | Mansmann | |
| 6,652,260 | B2 | 11/2003 | Nelson et al. | |
| 6,652,587 | B2 | 11/2003 | Felt et al. | |
| 6,942,475 | B2 | 9/2005 | Ensign et al. | |
| 6,998,134 | B2 | 2/2006 | Schmidmaier et al. | |
| 7,077,865 | B2 | 7/2006 | Bao et al. | |
| 7,087,200 | B2 | 8/2006 | Taboas et al. | |
| 7,264,825 | B2 | 9/2007 | Vogt et al. | |
| 7,306,610 | B2 | 12/2007 | Chern Lin et al. | |
| 7,320,709 | B2 | 1/2008 | Felt et al. | |
| 7,345,024 | B2 | 3/2008 | Vogt et al. | |
| 7,427,296 | B2 | 9/2008 | Evans | |
| 7,429,346 | B2 | 9/2008 | Ensign et al. | |
| 7,488,320 | B2 | 2/2009 | Middleton | |
| 7,601,176 | B2 | 10/2009 | Soffiati et al. | |
| 7,637,729 | B2 | 12/2009 | Hartman et al. | |
| 7,789,646 | B2 | 9/2010 | Haney et al. | |
| 7,799,084 | B2 | 9/2010 | Clemow et al. | |
| 7,842,095 | B2 | 11/2010 | Klein | |
| 7,867,426 | B2 | 1/2011 | Ziran et al. | |
| 7,914,582 | B2 | 3/2011 | Felt et al. | |
| 8,080,061 | B2 | 12/2011 | Appenzeller et al. | |
| 8,097,039 | B2 | 1/2012 | Evans | |
| 8,100,979 | B2 | 1/2012 | Felt et al. | |
| 8,206,143 | B2 | 6/2012 | Hawkins et al. | |
| 8,414,286 | B2 | 4/2013 | Haney et al. | |
| 8,449,621 | B2 | 5/2013 | Leonard et al. | |
| 8,480,389 | B2 | 7/2013 | Haney et al. | |
| 8,609,003 | B2 | 12/2013 | Vaidya | |
| 8,801,983 | B2 | 8/2014 | Haney et al. | |
| 8,834,772 | B2 | 9/2014 | Schindler et al. | |
| 8,852,187 | B2 | 10/2014 | Pool et al. | |
| 8,899,959 | B2 | 12/2014 | Haney et al. | |
| 8,920,152 | B2 | 12/2014 | Hawkins et al. | |
| 8,974,538 | B2 | 3/2015 | Teeny et al. | |
| 9,017,055 | B2 * | 4/2015 | Smith | B29C 39/26 249/91 |
| 9,056,011 | B2 | 6/2015 | Stolarski et al. | |
| 9,067,345 | B2 | 6/2015 | Hanke et al. | |
| 9,198,759 | B2 | 12/2015 | Faccioli et al. | |
| 9,278,002 | B2 | 3/2016 | Merrell et al. | |
| 9,295,554 | B2 | 3/2016 | Gillard et al. | |
| 9,415,134 | B2 | 8/2016 | Vogt | |
| 9,440,379 | B2 | 9/2016 | Smith et al. | |
| 9,452,001 | B2 | 9/2016 | Faccioli et al. | |
| 9,700,649 | B2 | 7/2017 | Vogt | |
| 9,707,008 | B2 | 7/2017 | Krebs et al. | |
| 9,770,273 | B2 | 9/2017 | Guitelman | |
| 9,770,355 | B2 | 9/2017 | Vogt et al. | |
| 9,775,595 | B2 | 10/2017 | Vogt | |
| 9,795,486 | B2 | 10/2017 | Faccioli et al. | |
| 9,814,499 | B2 | 11/2017 | Buscaglia et al. | |
| 9,819,161 | B2 | 11/2017 | Scirbona et al. | |
| 9,895,830 | B2 | 2/2018 | Vogt | |
| 9,925,363 | B2 | 3/2018 | Magagnoli | |
| 9,931,217 | B2 | 4/2018 | Kim | |
| 9,937,047 | B2 | 4/2018 | Holt et al. | |
| 9,944,000 | B2 | 4/2018 | Smith et al. | |
| 9,987,390 | B2 | 6/2018 | Vogt | |
| 9,993,340 | B2 * | 6/2018 | Foroni | B28B 7/00 |
| 10,022,235 | B2 | 7/2018 | Vogt | |
| 10,071,511 | B2 | 9/2018 | Smith et al. | |
| 10,238,436 | B2 | 3/2019 | Lawrence | |
| 10,401,569 | B2 | 9/2019 | Scirbona et al. | |
| 10,449,703 | B2 | 10/2019 | Smith et al. | |
| 10,498,118 | B2 | 12/2019 | Lu et al. | |
| 10,548,648 | B2 | 2/2020 | Buscaglia et al. | |
| 10,828,074 | B2 | 11/2020 | Jansen | |
| 2005/0107885 | A1 | 5/2005 | Evans | |
| 2005/0246025 | A1 | 11/2005 | Kyle | |
| 2006/0184250 | A1 | 8/2006 | Bandoh et al. | |
| 2007/0222114 | A1 | 9/2007 | Ziran et al. | |
| 2008/0058950 | A1 * | 3/2008 | Leonard | A61F 2/30 623/22.4 |
| 2009/0043307 | A1 | 2/2009 | Faccioli et al. | |
| 2009/0146342 | A1 * | 6/2009 | Haney | A61F 2/30942 425/111 |
| 2010/0137863 | A1 | 6/2010 | Munro | |
| 2010/0185298 | A1 | 7/2010 | Stone | |
| 2010/0318085 | A1 | 12/2010 | Austin et al. | |
| 2011/0158963 | A1 | 6/2011 | Font Pérez et al. | |
| 2012/0089148 | A1 | 4/2012 | Vaidya | |
| 2014/0017391 | A1 | 1/2014 | Smith et al. | |
| 2014/0277532 | A1 | 9/2014 | Teeny et al. | |
| 2015/0018828 | A1 | 1/2015 | Dorris | |
| 2015/0051539 | A1 | 2/2015 | Lin | |
| 2015/0250598 | A1 | 9/2015 | Yakimicki et al. | |
| 2015/0321389 | A1 | 11/2015 | Smith et al. | |
| 2016/0270919 | A1 | 9/2016 | Pastorino et al. | |
| 2016/0367371 | A1 | 12/2016 | De Beaubien et al. | |
| 2017/0173210 | A1 | 6/2017 | Vogt et al. | |
| 2018/0008325 | A1 | 1/2018 | Vaidya | |
| 2018/0339440 | A1 | 11/2018 | Smith et al. | |

FOREIGN PATENT DOCUMENTS

| | | | |
|---|---|---|---|
| CN | 104902851 | A | 9/2015 |
| CN | 106108998 | A | 11/2016 |
| CN | 205799989 | U | 12/2016 |
| CN | 109199562 | A | 1/2019 |
| EP | 2242451 | A1 | 10/2010 |
| EP | 2451493 | A2 | 5/2012 |
| EP | 2594297 | A1 | 5/2013 |
| EP | 2683312 | A1 | 1/2014 |
| EP | 3143963 | A1 | 3/2017 |
| EP | 3184126 | A1 | 6/2017 |
| EP | 3457992 | A1 | 3/2019 |
| JP | 2015-522359 | A | 8/2015 |
| WO | 98/51240 | A1 | 11/1998 |
| WO | 2004/082521 | A2 | 9/2004 |
| WO | 2005/034818 | A1 | 4/2005 |
| WO | 2009/076168 | A1 | 6/2009 |
| WO | 2011/004355 | A2 | 1/2011 |
| WO | 2012/120480 | A1 | 9/2012 |
| WO | 2013/041906 | A1 | 3/2013 |
| WO | 2014/093672 | A1 | 6/2014 |
| WO | 2017/070348 | A1 | 4/2017 |
| WO | 2017/199131 | A1 | 11/2017 |
| WO | 2018/049385 | A1 | 3/2018 |
| WO | 2018/175437 | A1 | 9/2018 |
| WO | 2018/227267 | A1 | 12/2018 |

(56) References Cited

FOREIGN PATENT DOCUMENTS

| | | | |
|---|---|---|---|
| WO | 2018/237288 | A1 | 12/2018 |
| WO | 2019/076420 | A1 | 4/2019 |

* cited by examiner

TEMPORARY ANTIMICROBIAL CEMENT SPACER, ASSEMBLY, KIT, AND METHOD OF MANUFACTURE

CROSS-REFERENCE TO RELATED APPLICATIONS

This application is a divisional application of U.S. Pat. No. 12,186,000, issued Jan. 7, 2025, from U.S. patent application Ser. No. 17/466,479, filed Sep. 3, 2021, which claims the benefit of U.S. Provisional Patent Application Ser. No. 63/074,516, filed Sep. 4, 2020, in the name of Navarro Vale et al., the entire disclosures of which are hereby incorporated by reference herein.

FIELD OF THE DISCLOSURE

The present disclosure is directed to temporary antimicrobial-eluting cement spacer implants, and assemblies, kits, and methods for forming the same. Particularly preferred disclosures are to modular spacer implants, assemblies, and kits, as well as methods of manufacturing the same, where the modular nature of the spacer permits the selection of specific desired length spacers, as well as specific selection of antimicrobial agent compounds and dosages, along with the components and processes for forming the same.

BACKGROUND

Currently in the United States there are no regulatorily approved products on the market indicated as a temporary intramedullary antimicrobial eluting spacer for treatment of localized infection of the intramedullary canal of a long bone like a tibia while providing a filling to the cavity created by the infected nail. Surgeons for many years have resorted to the use of off-label available products to fashion such an implant with limited stability as compared to intramedullary locking nails and limited control of the localized release rate of antimicrobial drug.

Current treatment protocol consists of poly (methyl methacrylate) (PMMA) cement mixed with antimicrobials to create a bone cement with drug eluting properties, which is then shaped using a chest tube or hand-rolled with an inserted metallic core for rigidity and anchorage. Handmade tibial spacer nails made intraoperatively have a number of issues including: time and complexity required to make the implant intraoperatively, possibility of cement fracture; lack of mechanism to capture fractured cement during removal; non-uniformity of implant from patient to patient; complexity of making implant; and, occasional need to remake implant due to insufficient or irregular cement coverage.

Thus, a need exists for a standardized treatment of care that will provide surgeons with the reliable ability to intraoperatively prepare antimicrobial-loaded cement intramedullary spacers, and reliably remove them when the infection treatment protocol has finished.

SUMMARY

Accordingly, the present disclosure is directed to the treatment of surgical site infections (SSIs) containing an infected implantable medical device. More specifically, the present disclosure is directed to temporary antimicrobial-eluting cement spacer implants, and assemblies, kits, and methods for forming the same. Particularly preferred disclosures are to modular spacers, assemblies, and kits, as well as methods of manufacturing the same, where the modular nature of the spacer permits the selection of specific desired length spacers, as well as specific selection of antimicrobial compounds and dosages, along with the components and processes for forming the same. A particular benefit is the ability of a surgeon, or other qualified healthcare professional, to perioperatively design a spacer that is specific to the needs of the particular patient conditions present at the time of surgery.

Typically, these temporary spacer implants are used in cases of infected orthopedic implants where revision surgery will be necessary; for example, intramedullary nails used in the femur or tibia.

According to the present disclosure, an antimicrobial eluting temporary cement spacer is disclosed, the temporary cement spacer including:

- a spacer core including
  - a rod defining a central axis of the spacer core and having a proximal rod end and a distal rod end opposite the proximal rod end along the central axis, the rod further defining an outer rod surface extending between the proximal rod end and the distal rod end;
  - a locking component defining a distal locking end and a proximal locking end opposite the distal locking end along the central axis, the distal locking end attached to the rod at the proximal rod end, the locking component further defining at least one locking bore extending through the locking component in a radial direction with respect to the central axis, the at least one locking bore configured to receive a locking screw; and,
  - a cap defining a proximal cap end and a distal cap end opposite the proximal cap end along the central axis, the proximal cap end attached to the distal rod end; and,
- a cement coating surrounding at least a portion of the outer rod surface, the cement coating comprising a mixture of a cement material and one or more antimicrobial agents;
  - wherein the cap is configured to define the leading end of the temporary spacer during implantation.

According to certain embodiments, the outer rod surface includes a threaded surface at the proximal rod end, and wherein the distal locking end defines a distal locking opening configured to threadingly engage with the proximal rod end. In additional embodiments, the outer rod surface includes a threaded surface at the distal rod end, and wherein the proximal cap end defines a proximal cap opening configured to threadingly engage with the distal rod end. In still further embodiments, the outer surface of the rod includes a continuously threaded surface extending from the distal rod end to the proximal rod end.

According to certain embodiments, the at least one locking bore includes a plurality of locking bores.

According to certain embodiments, the locking component extends in axial direction from the distal locking end to the proximal locking end such that the proximal locking end can be angular offset in a radial direction with respect to the central axis by an angle theta, θ. In certain embodiments, the angular offset angle is in the range of about 5 degrees to about 20 degrees.

In certain embodiments, the cap defines a cross-sectional area in a plane perpendicular to the central axis, and wherein the cap cross-sectional area defines the maximum cross sectional area of the temporary spacer.

According to certain embodiments, the temporary spacer includes one or more centering members extending radially outward from the outer rod surface. In further embodiments, each centering member of the one or more centering members defines four arms, each arm extending radially outward from the outer rod surface.

According to additional embodiments, the locking component defines an outer locking surface extending from the proximal locking end to the distal locking end. In further embodiments, the outer locking surface can define at least one planar portion extending in a direction from the proximal locking end to the distal locking end. In still further embodiments, the at least one planar portion includes a plurality of planar portions, each of the plurality of planar portions spaced equidistant from another of the planar portions along the outer locking surface.

According to yet additional embodiments, the outer locking surface further defines at least one surface channel extending in a direction from the proximal locking end to the distal locking end. In certain additional embodiments, the at least one surface channel is directly adjacent to at least one of the at least one planar portions. According to certain embodiments, the at least one surface channel includes a plurality of surface channels such that each surface channel of the plurality of surface channels is directly adjacent to the at least one planar portion.

According to certain embodiments, the cap defines a plurality of fenestrations extending through the cap in a direction generally coaxial with the central axis from the distal cap end to the proximal cap end. In certain embodiments, the plurality of fenestrations are evenly distributed around the cap.

According to certain embodiments, the curable polymer material comprises poly (methyl methacrylate) (PMMA) or a copolymer thereof.

According to certain embodiments, the antimicrobial agent comprises antibiotics, antifungals, or combinations thereof. For example, certain suitable antibiotic classes can include aminoglycosides and glycopeptides. Specific agents can include, for example, gentamicin, tobramycin, vancomycin, amikacin, rifampin, clindamycin, erythromycin, colistin, linezolid, daptomycin, fosfomycin, and amphotericin B, or combinations thereof. Preferred agents can include gentamicin, tobramycin, and vancomycin, or combinations thereof.

According to certain embodiments, the rod comprises a metal or metal alloy, or a thermoplastic polymer material. According to further embodiments, the locking component comprises a metal or metal alloy, or a thermoplastic polymer material. In still further embodiments, the cap comprises a metal or metal alloy, or a thermoplastic polymer material.

According to the present disclosure, a mold assembly for forming the temporary cement spacer is disclosed including:

- a spacer core including
  - a rod defining a central axis of the mold assembly and having a proximal rod end and a distal rod end opposite the proximal rod end along the central axis, the rod further defining an outer rod surface extending between the proximal rod end and the distal rod end;
  - a locking component defining a distal locking end and a proximal locking end opposite the distal locking end along the central axis, the distal locking end attached to the rod at the proximal rod end, the locking component further defining at least one locking bore extending through the locking component in a radial direction with respect to the central axis, the at least one locking bore configured to receive a locking screw; and,
- a mold body extending along the central axis, the mold body defining a proximal mold end and a distal mold end opposite the proximal mold end along the central axis, the proximal mold end including a proximal mold opening and the distal mold end including proximal mold opening, wherein the mold body defines an inner mold surface extending between the proximal mold opening and the distal mold opening, wherein the inner surface defines a mold lumen, wherein the spacer core is disposed within the mold lumen such that the locking component is disposed within the mold lumen at the proximal mold end;
- at least one bore plug disposed in the at least one locking bore; and,
- an adapter configured to operably couple to the mold body at the distal mold end, the adapter configured to operably couple the mold body to a bone cement injection device so as to provide a fluid pathway from the cement injection device through the distal mold opening to the mold lumen.

According to certain embodiments, the at least one locking bore includes a plurality of locking bores. In certain embodiments, the at least one bore plug comprises a plurality of bore plugs. In certain additional embodiments, each locking bore of the plurality of locking bores has a bore plug of the plurality of bore plugs disposed within it such that an amount of the plurality of locking bores is equal to an amount of the plurality of bore plugs. In alternative embodiments, a first portion of the plurality of locking bores has the plurality of bore plugs disposed within it, and wherein a second portion of the plurality of locking bores do not have the plurality of bore plugs disposed within it.

According to certain embodiments, the mold body further comprises at least one mold bore, the at least one mold bore extending through the mold body and the mold lumen in a radial direction with respect to the central axis, and wherein the at least one bore plug is configured to be disposed in the at least one mold bore. In certain embodiments, the at least one mold bore is aligned with the at least one locking bore such that the at least one bore plug can be disposed within both the at least one locking bore and the at least one mold bore. In certain embodiments, the at least one mold bore comprises a plurality of mold bores.

According to certain embodiments, the mold body includes separation means extending along the mold body in an axial direction from the proximal mold end to the distal mold end. In certain embodiments, the mold body further defines an outer mold surface extending between the proximal mold end and the distal mold end, and wherein the separation means include a plurality of perforations in the outer mold surface, a groove in the outer mold surface, or a strip of material disposed within the mold body, or a combination thereof. In certain embodiments, the mold body further comprises one or more reinforcing members. In still further embodiments, the mold assembly further includes one or more tabs disposed at either the proximal mold end or the distal mold end of the mold body.

According to certain embodiments, the spacer core further comprises a cap configured to operably couple to the distal rod end.

According to certain embodiments, the adapter defines a proximal end operably coupled to the distal end of the mold body and defining a proximal opening. Additionally, the adapter further defines an opposing distal end configured to operably couple to the bone cement injection device and having a distal opening such that the adapter comprises an adapter recess extending between the distal opening and the proximal opening that provides the continuous fluid pathway. In certain additional embodiments, the adapter comprises an inner wall, the inner wall defining an adapter receptacle having a receptacle opening, and wherein the distal end of the rod is disposed in the adapter receptacle.

According to certain embodiments, the mold assembly further includes a cap configured to operably couple to the distal end of the spacer core. In certain embodiments, the cap defines a plurality of fenestrations extending axially through the cap from a distal cap end to a proximal cap end.

According to the present disclosure, a kit for forming a temporary cement spacer is disclosed, the kit including:

at least one rod defining a proximal rod end and a distal rod end opposite the proximal rod end;

a locking component configured to operably couple to the rod, the locking component defining a distal locking end and a proximal locking end opposite the distal locking end, the distal locking end configured to attach to the rod at the proximal rod end, the locking component further defining at least one locking bore extending through the locking component and configured to receive a locking screw, wherein the at least one rod and the locking component are configured to form a spacer core when operably coupled;

at least one bore plug configured to be removably disposed within the at least one locking bore;

a mold body defining a proximal mold end and a distal mold end opposite the proximal mold end and an outer mold surface extending from the proximal mold end and the distal mold end, the mold body further defining a proximal mold opening at the proximal mold end and a distal mold opening at the distal mold end and an inner mold surface extending between the proximal mold opening and distal mold opening, the inner mold service defining a mold lumen extending therebetween, wherein the spacer core is configured to be disposed in the mold lumen;

an adapter configured to operably couple to the mold body at the distal mold end, wherein the adapter is further configured to couple a bone cement injection device to the distal mold opening so as to provide a fluid pathway from the cement injection device to the mold lumen; and, a cap configured to operably couple to the distal rod end.

According to certain further embodiments, the at least one rod comprises a plurality of rods, wherein each rod of the plurality of rods has a length measured between the proximal rod end and the distal rod end, and wherein each rod length is different than any other rod length of the plurality of rods. In certain embodiments, the at least one rod defines an outer rod surface extending from the proximal rod end to the distal rod end, and further wherein the outer rod surface comprises a continuously threaded surface.

According to certain embodiments, the at least one bore plug comprises a plurality of bore plugs.

According to certain embodiments, the kit further includes at least one locking bone screw, wherein the at least one locking screw is configured to be disposed in the at least one locking bore and further configured to secure the temporary spacer to bone.

According to certain embodiments, the kit includes an insertion instrument, the insertion instrument configured to operably couple to the proximal end of the locking component, wherein the insertion instrument is configured for implanting the temporary spacer.

According to the present disclosure, a method of forming an antimicrobial eluting temporary cement spacer is described, the method including the steps of:

inserting a spacer core into a lumen of a mold body, the spacer core including a rod and a locking component connected to the rod, wherein the locking component includes at least one locking bore;

coupling a bone cement injection device to the mold body with an adapter to provide a fluid pathway from the bone cement injection device into the mold body lumen;

disposing at least one bore plug into the at least one locking bore;

injecting bone cement material including one or more antimicrobial agents into the mold body lumen through the fluid pathway and along at least a portion of an outer surface of the rod;

curing the bone cement material on the outer rod surface so as to form a cement coating on the spacer core, whereby the antimicrobial eluting temporary cement spacer is formed;

decoupling the bone cement injection device from the mold body;

removing the at least one bore plug from the at least one locking bore; and, separating the mold body from the antimicrobial eluting temporary cement spacer.

According to certain embodiments, the method further comprises prior to the step of inserting the spacer core into the mold lumen, connecting the rod to the locking component. In certain embodiments, the method further includes operably coupling a proximal end of the rod to a distal end of the locking component.

According to certain embodiments, the rod has a rod length measured from a proximal rod end to an opposing distal rod end, the method further includes, prior to the step of inserting the spacer core, removing a portion of the rod length from either the proximal rod end or the distal rod end.

According to additional embodiments, the mold body defines a mold length measured from a proximal mold end to an opposing distal mold end, and the method includes removing a portion of the mold body length from either the proximal mold end or the distal mold end.

According to certain embodiments, the mold body defines an outer mold surface extending from the proximal mold end to the distal mold end, and the mold body includes at least one mold bore extending from the outer mold surface through the mold lumen, the method includes aligning the at least one locking bore with the at least one mold bore. According to further embodiments, the step of disposing the at least one bore plug into the at least one locking bore further includes disposing the at least one bore plug in the at least one mold bore.

According to certain embodiments, the methods can further include attaching a cap to the rod. In additional embodiments, the step of attaching the cap occurs after the step of decoupling the mold body from the bone cement injection device.

In certain further embodiments, the cap defines a proximal cap end and an opposing distal cap end, the proximal cap end is operably coupled to a distal end of the rod, the cap comprises a plurality of fenestrations extending through the cap from the distal cap end to the proximal cap end, and the plurality of fenestrations are configure to provide a fluid pathway from the cement injection device into the mold lumen, the method can further include injecting bone cement material includes injecting bone cement material through the cap fenestrations into the mold lumen.

DETAILED DESCRIPTION

Figure 1A:
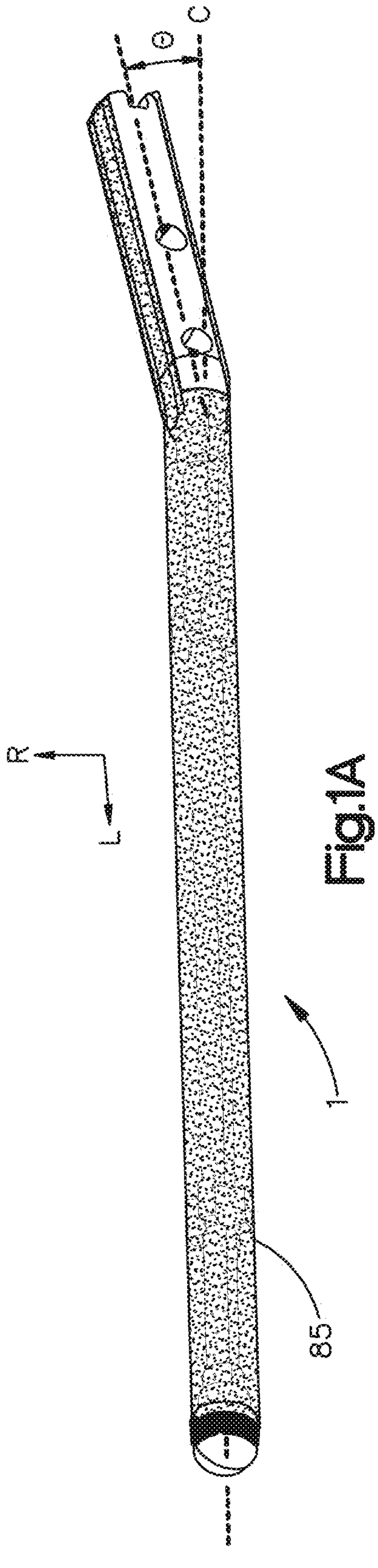
FIG. 1A is a side view photograph of a temporary cement spacer according to embodiments of the present disclosure.

The present disclosure is directed to temporary antimicrobial-eluting cement spacer implants, and assemblies, kits, and methods for forming the same for the use in the treatment of surgical site infections (SSIs). Typically, these temporary spacer implants are formed with an antimicrobial agent mixed into a polymer or ceramic cement material, and are used in cases of infected orthopedic implants where revision surgery will be necessary; for example, intramedullary nails used in the femur or tibia. The temporary spacer generally approximates the shape of the removed infected implant. Once the infected implant is removed, the temporary antimicrobial-eluting spacer implant is inserted into the same location and the cement material including the antimicrobial agent provides a local drug depot that elutes the antimicrobial agent to reduce the infection and prevent bacterial growth on the spacer at the implant site. Once the infection has been resolved, the temporary spacer is removed, and a new permanent revision implant is then placed in that location.

The present disclosure is particularly directed to modular temporary spacers, where the modular nature of the spacer permits both the selection of specific desired length spacers, as well as specific selection of antimicrobial compounds and dosages to be mixed into the cement material. Additionally, the temporary cement spacer can be utilized with locking screws to secure the spacer into adjoining bone, which provides the benefit of maintaining the position and stability of the temporary spacer in the desired location. In essence, the temporary spacers of the present disclosure are customizable to the specific criteria of the individual patient and can be properly secured once implanted. An additional benefit is the ability of a surgeon, or other qualified healthcare professional, to perioperatively design and form a temporary spacer according to the present disclosure at, or near, the time of surgery. Thus, the surgeon can evaluate the circumstances at the time of removing the infected implant and contemporaneously prepare a temporary spacer implant to most appropriately address the surgical site conditions.

As will be described in greater detail below, the present disclosure includes assemblies and kits including a mold body and spacer core that are used in forming the temporary spacer. The mold body has a lumen configured to house the spacer core and receive an injected antimicrobial cement material, which will cure and harden forming a cement coating around the spacer core, and thus the mold body is configured to substantially define the shape of the temporary spacer. The present disclosure additionally describes methods of forming the temporary spacer utilizing the mold body, the spacer core, and the antimicrobial cement material.

Words and phrases representing anatomical references, such as “proximal” and “distal” may be used throughout this disclosure in reference to both the implant, assemblies, kits, and methods described herein, as well as a patient’s natural anatomy. Such terms have well-understood meanings in both the study of anatomy and the field of orthopedics. Use of such terms in the specification and claims is intended to be consistent with their well-understood meanings unless noted otherwise.

According to the present disclosure, and with reference to FIGS. 1A-1D, an antimicrobial eluting temporary spacer 1 is disclosed, the temporary spacer 1 including a spacer core 5 and an antimicrobial cement coating 85 surrounding at least a portion of the spacer core 5. The cement coating 85 includes a cement material comprising a curable polymer material or curable ceramic material, mixed with one or more antimicrobial agents, and is configured for use in treatment of an infection. The temporary spacer core 5 is configured to provide the structural framework of the temporary spacer 1, and includes a rod 20, a locking component 40, and a cap 60. The locking component 40 and the cap 60 are configured to couple to opposing ends (i.e., proximal and distal ends) of the rod 20 as will be explained in greater detail below.

According to certain embodiments, the curable polymer material comprises poly (methyl methacrylate) (PMMA) or a copolymer thereof.

According to certain embodiments, the antimicrobial agent comprises antibiotics, antifungals, or combinations thereof. For example, certain suitable antibiotic classes can include aminoglycosides and glycopeptides. Specific agents can include, for example, gentamicin, tobramycin, vancomycin, amikacin, rifampin, clindamycin, erythromycin, colistin, linezolid, daptomycin, fosfomycin, and amphotericin B, or combinations thereof. Preferred agents can include gentamicin, tobramycin, and vancomycin, or combinations thereof.

According to certain embodiments, the rod 20 comprises a metal or metal alloy, or a thermoplastic polymer material. According to further embodiments, the locking component 40 comprises a metal or metal alloy, or a thermoplastic polymer material. In still further embodiments, the cap 60 comprises a metal or metal alloy, or a thermoplastic polymer material. Suitable metals can include, for example, standard orthopedic implant grade metals or alloys such as 316L stainless steel, titanium, Ti-6Al-4V alloy, Ti-6Al-7Nb alloy, or cobalt-chrome alloys. Suitable thermoplastics can include, for example, any polymer or co-polymer of the polyaryletherketone family, such as polyetheretherketone (PEEK), as well as polyethylene, polypropylene, or nylon.

With reference to FIGS. 1A-D, the rod 20 is elongate in a longitudinal direction L and defines a central axis C of both the spacer core 5 and the temporary spacer 1 that extends in the longitudinal direction. As used herein, terms such as “axial” or “axially” or derivatives thereof are intended to define a directional component that is substantially or completely co-extensive with the central axis C.

The rod 20 further defines a proximal rod end 22 and a distal rod end 24 opposite the proximal rod end 22 along the central axis C and an outer rod surface 26 extending from the proximal rod end 22 to the distal rod end 24.

The rod 20 is configured to attach to the locking component 40 at the proximal rod end 22. The rod 20 is additionally configured to attach to the cap 60 at the distal rod end 24. Accordingly, with reference to FIG. 1C, a portion of the outer rod surface 26 at the proximal rod end 22 can be configured as a threaded surface 28 such that it can threadingly engage with the locking component 40. Additionally, a portion of the outer rod surface 26 at the distal rod end 24 can be configured as a threaded surface 28 such that it can threadingly engage with the cap 60. Alternatively, and with reference to FIG. 1D, substantially an entirety of the outer rod surface 26 can be configured as a threaded surface 28. As used herein with respect to the threaded surface 28, “substantially” means a range of at least 50% up to 100% (such as 50%, 60%, 70%, 80%, 90%, or 100%, or any suitable subrange derivable from the percentages listed herein) of the outer rod surface 26 is a threaded surface 28. For example, as shown FIG. 1D, 100% of the outer rod surface 26 is configured as a threaded surface 28, such that it can be said that the outer rod surface 26 is a continuously threaded surface 28 extending from the distal rod end 24 to the proximal rod end 22. This particular example of a continuously threaded rod 20 provides a benefit with regards to the modular nature of the temporary spacer 1 that was previously described. With a continuously threaded rod 20, a surgeon can cut the rod 20 to any desired length and still maintain threaded surfaces 28 at both the proximal rod end 22 and the distal rod end 24 to threadingly engage with both the locking component 40 and cap 60, respectively.

With reference to FIGS. 1B-2C, the spacer core 5 includes a locking component 40 configured to attach to the rod 20 at the proximal rod end 22. The locking component 40 is configured to provide the structure for locking screws to secure the temporary spacer 1 to adjoining bone as will be explained in greater detail below. The locking component 40 is generally elongate in the axial direction (i.e., elongate along the central axis C in the same direction as the rod 20). The locking component 40 includes a distal locking end 44 configured to attach to the proximal rod end 22, and a proximal locking end 42, opposite the distal locking end 44 along the central axis C. An outer locking surface 46 extends from the proximal locking end 22 to the distal locking end 46.

The distal locking end 46 is configured to operably couple to the proximal rod end 22 and can include a distal locking opening 32 and an inner distal locking surface 33 that defines a distal locking recess 35 extending proximally from the distal locking opening 32 towards the proximal locking end 42. The distal locking recess 35 is configured to receive the proximal rod end 22 such that when the rod 20 is operably coupled to the locking component 40, the proximal rod end 22 is disposed, at least partially, in the distal locking recess 35. In certain examples, such as shown in FIG. 2A, the inner distal locking surface 33 can be threaded and configured to threadingly connect with a corresponding threaded surface 28 of proximal rod end 22 as has been previously described.

Figure 1B:
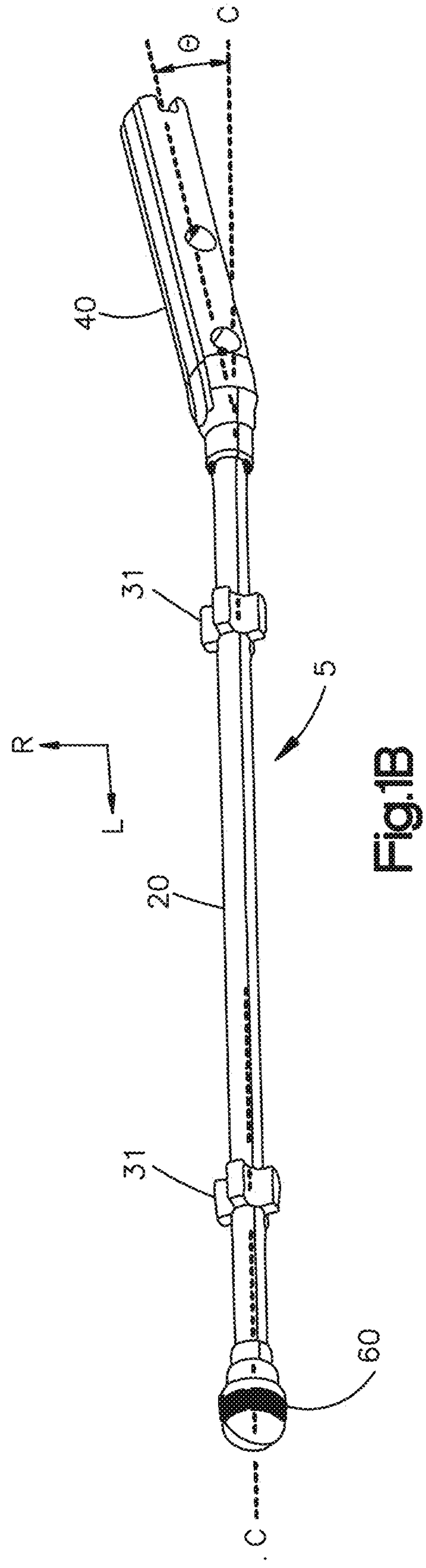
FIG. 1B is a side view of a spacer core including a rod, a locking component, and cap, according to certain embodiments.
Figure 1C:
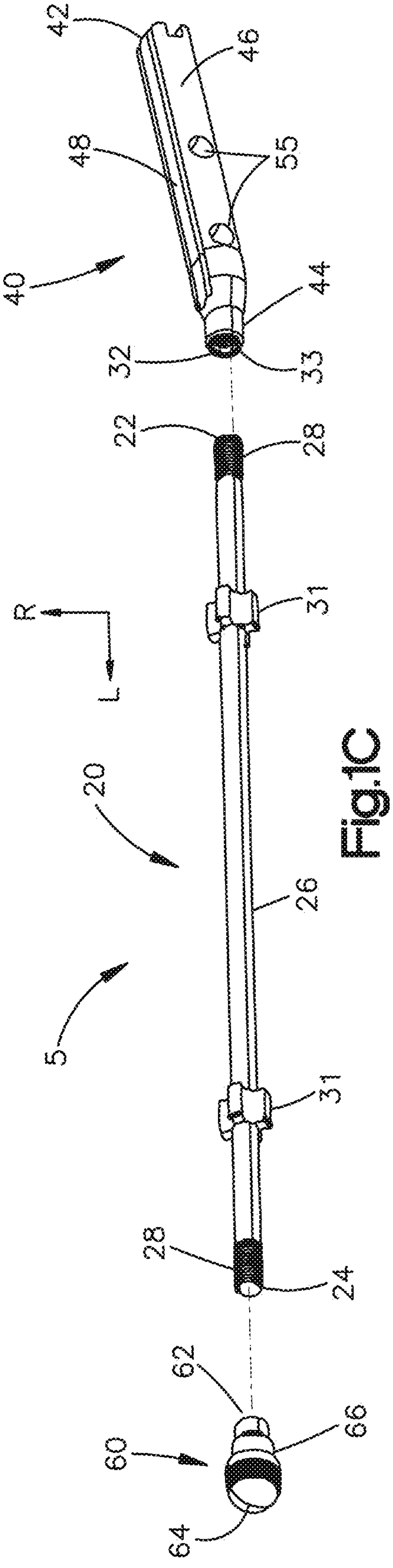
FIG. 1C is an exploded view of the spacer core according to FIG. 1B showing threaded outer surface at the proximal and distal ends of the rod.
Figure 1D:
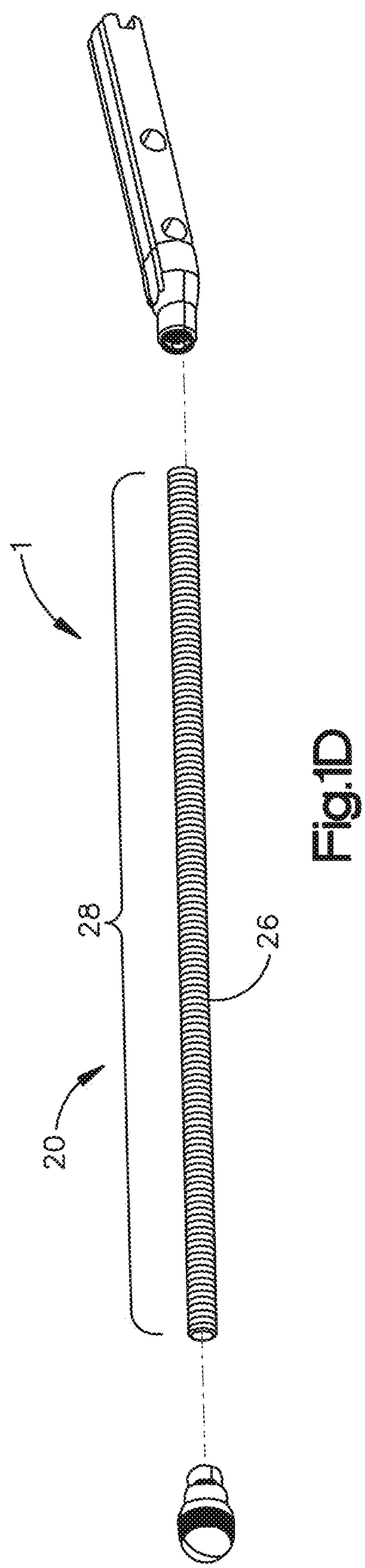
FIG. 1D is an exploded view of an alternate embodiment showing an entirely threaded outer surface of the rod.
Figure 2A:
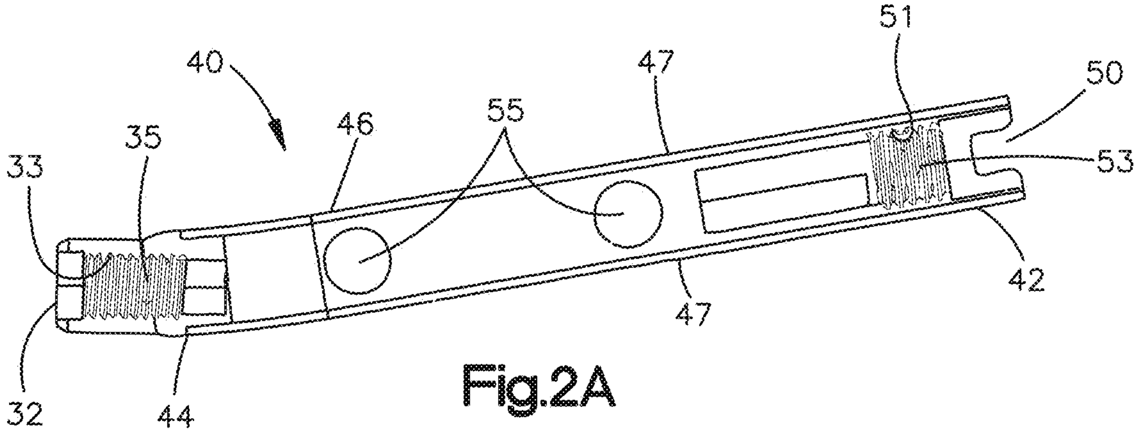
FIG. 2A is cross-section side view of the locking component shown in FIG. 1C.
Figure 2B:
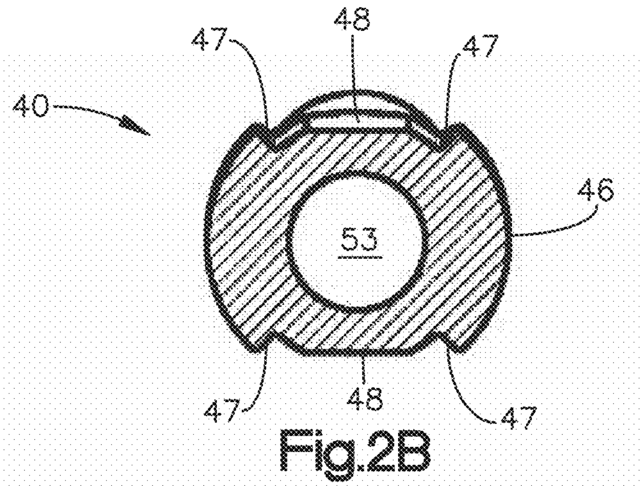
FIG. 2B is a cross-section of the locking component shown in FIG. 1C viewed from the proximal end.
Figure 2C:
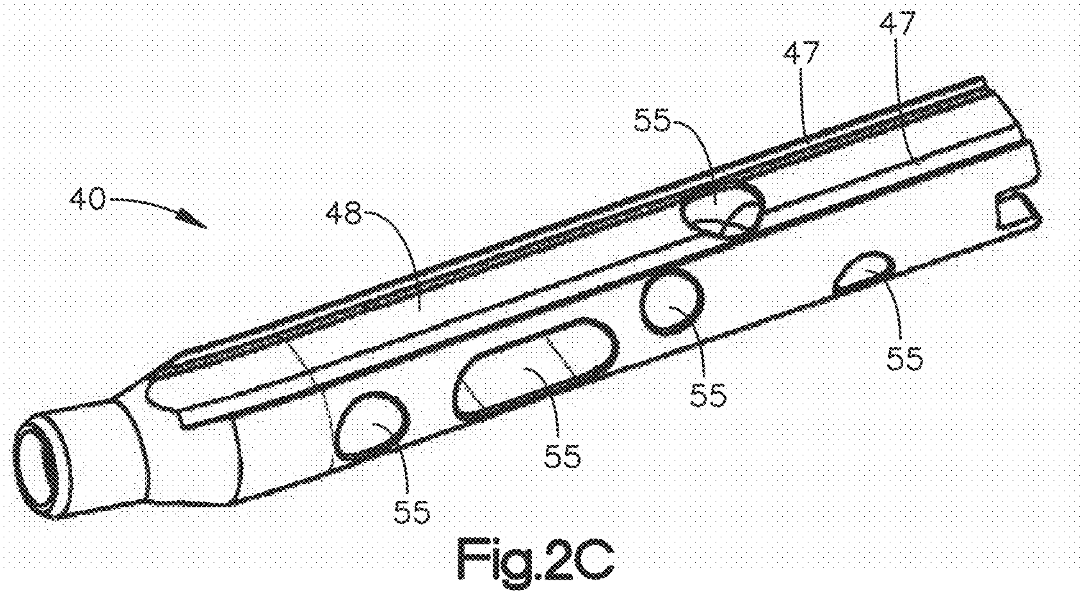
FIG. 2C is a perspective view of an alternate locking component showing multiple offset radial bores.

With reference to FIGS. 1C, 2A, and 2C, the locking component 40 includes at least one locking bore 55 that is configured to receive a locking screw, which can secure the temporary spacer 1 to adjoining bone. Locking screws are well-known in the field of orthopedic implants and are used to pass through an opening in the implant and secured into the bone adjacent to the implant. One benefit of utilizing a locking component 40 including at least one locking bore is the ability to provide a level of stability once it is implanted into the patient through the use of the locking screws. While the use of the locking screws is not intended to provide weight-bearing stability as they would in a standard orthopedic implant, the ability to partially stabilize the temporary spacer 1 minimizes the chances of it being damaged or otherwise migrating from its intended location during the time it is implanted in the patient.

With continued reference to FIGS. 1C, 2A, and 2C, the at least one locking bore 55 of the locking component 20 extends in a radial direction R with respect to central axis C through locking component 40. As used herein, terms such as "radial" or "radially" or derivations thereof are directions or locations defined with respect to the central axis C and can include radially inward direction towards the central axis C as well as radially outward direction away from the central axis C. In certain examples, the radial direction is oriented perpendicular to the central axis C and in other examples the radial direction can be angularly offset from a direction that is perpendicular to the central axis C but is not coaxial or parallel with the central axis C. Preferably, the radial extension of at least one locking bore 55 is perpendicular with respect to the central axis C.

With reference to FIGS. 1C-1D and FIGS. 2A and 2C, the at least one locking bore 55 can comprise a plurality of locking bores 55, such as two, three, four, five, up to six locking bores 55. The advantage of a plurality of locking bores 55 is that it can provide a surgeon with multiple approaches for securing the temporary spacer 1 to adjoining bone with the locking screw or multiple locking screws as desired. It should be appreciated that the anatomical region receiving the temporary spacer 1 has already been subject to an invasive infection as well as the morbidity associated with the removal of the infected primary implant. As such there is likely to be tissue damage, particularly damaged bone tissue in the area where a surgeon would normally attempt to secure the temporary spacer 1 with a locking screw. Thus, providing multiple options to locate healthy bone tissue for securement is a benefit to the surgeon in successfully implanting the temporary spacer 1.

Figure 11:
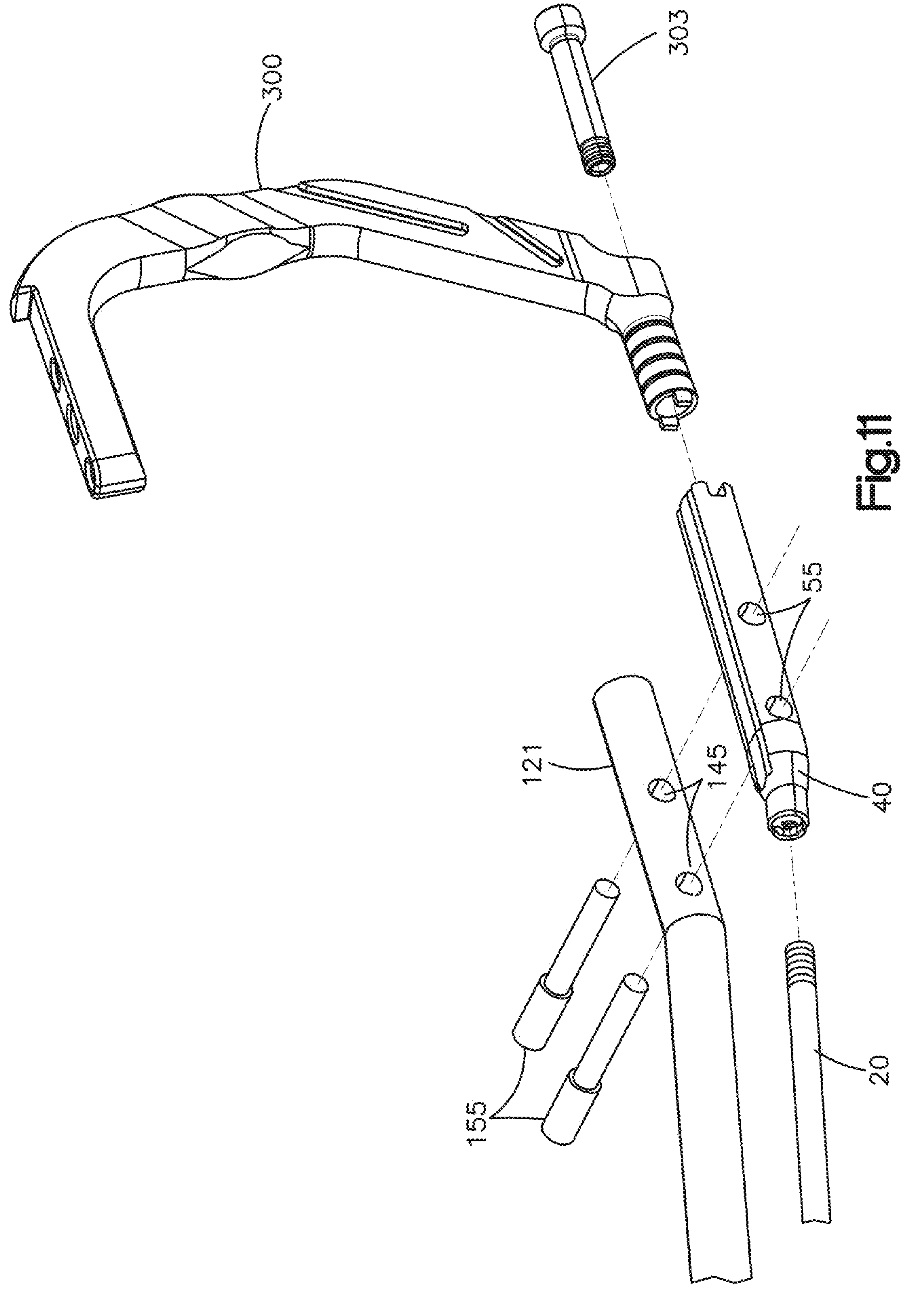
FIG. 11 is a perspective exploded view of the proximal end of the mold body assembly of FIG. 5A shown with an insertion handle.

The locking component 40 can be further configured to engage with one or more insertion instruments that aid a surgeon or other medical professional in the placement of the temporary spacer 1 into the desired anatomical location of the patient. In one example, as shown in FIG. 2A, the proximal locking end 42 includes a proximal locking opening 50 and a proximal locking inner surface 51 defining a proximal locking recess 53 extending distally from the proximal locking opening 50 towards the distal locking end 44. In certain examples, such as is shown in FIG. 11 and explained in further detail below, the proximal locking end 42 is configured to receive an insertion instrument 300 within the proximal locking recess 53. In certain examples, the proximal locking inner surface 51 can be threaded and configured to threadingly connect with a corresponding threaded component or surface of the insertion instrument 300.

In certain examples, such as shown in FIG. 1B, the locking component 40 can extend axially from the distal locking end 44 to the proximal locking end 42 such that the proximal locking end 42 can be radially offset from the distal locking end 44 with respect to the direction of the central axis C by an angle theta θ. The purpose of the angular offset is to, where appropriate, better align the shape of the temporary spacer 1 with the natural anatomy of the bone of the patient in which the temporary spacer 1 will be implanted both in regards to the step of inserting the temporary spacer 1, as well as maintaining proper anatomical alignment after implantation is completed. In certain embodiments, the angular offset, θ, can be anywhere in the range of about 5 degrees to about 20 degrees, for example in the range of about 5 degrees to about 15 degrees, or about 8 degrees to 12 degrees, or any subcombination of the range endpoints listed here.

With reference to FIGS. 1B-1D and FIGS. 3-4B, the cap 60 defines a proximal end 62 that is configured to attach to the rod 20 at the distal rod end 24. The cap 60 further defines a cross-sectional area measured in a plane perpendicular to central axis C and the cap 60 cross-sectional area can define the maximum cross-sectional area of the temporary spacer 1. In other words, the cap 60 is designed to preferably be the widest portion of the temporary spacer 1, although in other embodiments the locking component can define the maximum cross-sectional area of the temporary spacer 1. The cap 60 defining the maximum cross-sectional area provides two benefits. First, during implantation, the cap 60 is configured to be the leading end of the temporary spacer 1 and as such can be frequently subject to significant mechanical forces, such as compressive and shear forces. Thus, the cap 60 provides a forward buttress to absorb those forces and clear a path as the temporary spacer 1 penetrates into the desired anatomical location. This protects portions of the cement coating 85 from fracturing or otherwise dislodging from the temporary spacer 1 and damaging the functionality of the temporary spacer 1 in vivo. Second, as previously described, the temporary spacer 1 of the present disclosure require explanation once the clinically proscribed antimicrobial treatment period has expired. The function of the cap 60 during explanation is to collect any cement coating 85 debris that was created. In other words, the cap 60 is preferably designed such that when the temporary spacer 1 is removed from the patient, cap 60 functions to force upwards (or collect) any broken cement fragments from the cement coating 85 that had become dislodged or fractured during, or prior to, explanation of the temporary spacer 1.

Figure 3:
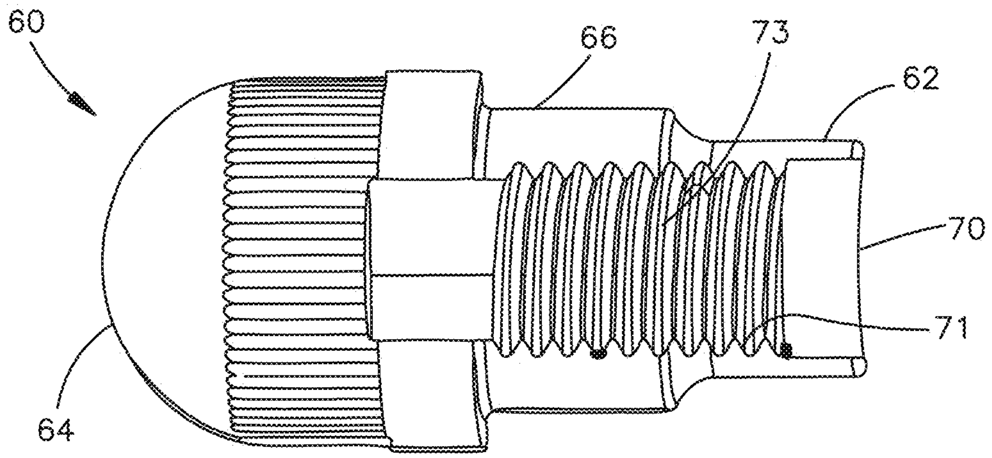
FIG. 3 is a cross-section side view of the cap shown in FIG. 1B.
Figure 4A:
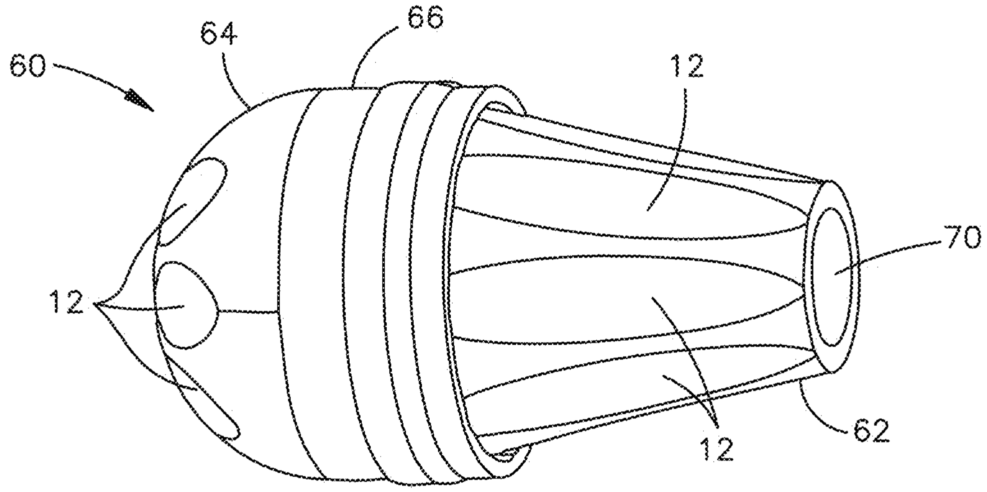
FIG. 4A is side view of an alternate embodiment of the cap of FIG. 3 showing a plurality of axial fenestrations.
Figure 4B:
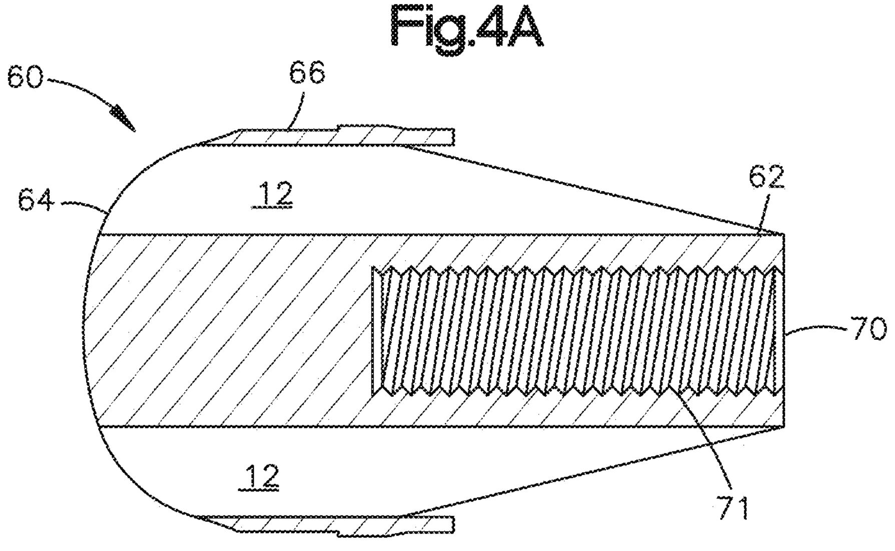
FIG. 4B is a cross-section side view of the cap of 4A.

With continued reference to FIG. 3 and FIGS. 4A-4B, the cap 60 includes a distal cap end 64, opposite the proximate cap end 62 along the central axis C. An outer cap surface 66 extends from the proximal cap end 62 to the distal cap end 64. The proximal cap end 62 includes a cap opening 70 and an inner cap surface 71 that defines a cap recess 73 that extends into the cap 60 in a distal direction D from the cap opening 70 towards the distal cap end 64, such that it can be said the cap recess 73 extends distally from the cap opening 70. The cap recess 73 is configured receive the distal rod end 24 such that, when coupled, the distal rod end 24 is, at least partially, disposed in the cap recess 73. In certain examples, such as is shown in FIGS. 3 and 4B, the inner cap surface 71 can be threaded and configured to threadingly connect with a corresponding threaded surface 28 of distal rod end 24.

Figure 5A:
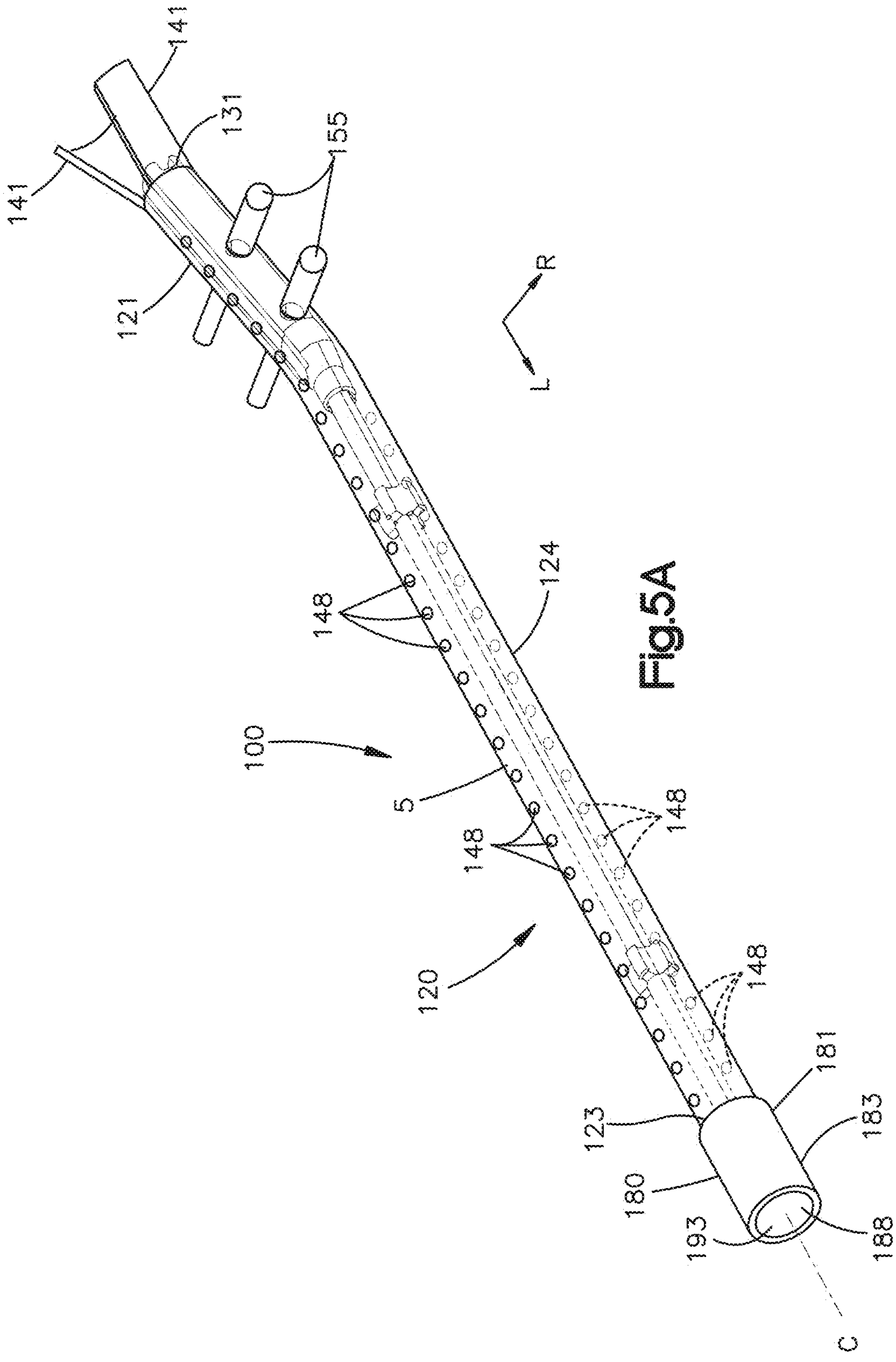
FIG. 5A is perspective view of a mold assembly according to embodiments of the present disclosure.

With reference to FIGS. 1B-1C, in certain examples, the spacer core 5 of the temporary spacer 1 can include one or more centering members 31 extending radially outward from the outer rod surface 26. As will be explained in greater detail below, a mold assembly 100 is disclosed where the spacer core 5 is configured to be inserted into a mold body 120 in order to form the temporary spacer 1, for example, such as shown in FIG. 5A. Thus, in certain examples, there are elements of the spacer core 5 that function to interact with the mold body 120 in forming the temporary spacer 1. In certain embodiments, the centering members 31 can be attached to the rod 20, and in alternative embodiments, the rod 20 and the centering members 31 can be formed as a single monolithic structure. Centering members 31 function to provide an offset between the rod 20 and the mold body 120 and keep the rod 20 aligned along central axis C when it is disposed in the mold body 120 (for example, as shown in FIG. 5A) This alignment of the rod 20 longitudinally along central axis C assists in forming a uniform distribution of the cement material used to form cement coating 85 around spacer core 5 because the rod 20 will be centered within the mold body 120.

The centering members 31 can include at least a single arm that extends radially outward from the rod 20. For instance, each of the centering members 31 can include a plurality of arms. The arms of the centering members 31 can be circumferentially spaced apart from one another about the outer surface. For example, as shown in FIGS. 1B-1C, (and FIGS. 5A-5B) two centering members 31 are attached to rod 20 and have a substantially cross-shaped (or X-shape) cross-section, with four (4) arms extending radially outward from rod 20. This cross-shaped design provides spaces between the arms of the centering members to allow cement material to flow past the centering members 31 and coat the outer rod surface 26 during the process of forming the cement coating 85. It should also be appreciated that the centering members 31 may assume any suitable cross-sectional geometry provided that they do not block, or otherwise inhibit, the flow of the fluid cement material.

As previously described, the temporary spacers 1 of the present disclosure are designed to have a modular functionality that allows for a desired length of rod 20 to be used by a surgeon depending upon the specific conditions of the patient's anatomy. As such, it should be appreciated that more or less than two centering members 31 may extend from the rod 20 depending on the desired selected length of the rod 20. For example, 1, 2, 3, 4, 5, or up to 8 centering members 31 could extend outward from the rod 20.

With reference to FIGS. 1B-C and FIGS. 2A-C, the outer locking surface 46 can define at least one planar portion 48 extending in a direction from the proximal locking end 42 to the distal locking end 44. This is an additional element of the spacer core 5 that is configured to function with the mold body 120 to form the temporary spacer 1. A potential benefit to the planar portion 48 is that it creates a gap or void between the mold body 120 and the locking component 40 when the spacer core 5 is disposed within the mold body 120. This gap or void provides a space for access along a portion of the outer locking surface 46 when cement material is injected into the mold body 120 for forming the cement coating 85. In certain examples, as shown in FIG. 2B, the outer locking surface 46 can include a plurality of planar surfaces 48, for example, two planar portions 48. In a preferred embodiment, the planar portions 48 are disposed equidistant from one another on the locking outer surface 46.

In certain further embodiments, and with continued reference to FIGS. 2A-C, the outer locking surface 46 can define at least one surface channel 47 extending in a direction from the proximal locking end 42 to the distal locking end 44. An advantage to including surface channel 47 along the outer surface 46 is that as the fluid cement material that forms cement coating 85 flows into the mold body 120, it can fill the at least one surface channel 47 and harden, and once hardened it will provide resistance to forces acting on the cement coating 85 during implantation or explanation (e.g. torsion) that could cause fracture or delamination of the cement coating 85 from the locking component 40. In other words, portions of the cement coating 85 are shielded within the surface channel 47 from the mechanical forces that occur during implantation and explanation that can inadvertently pry, dislodge, or fracture the cement coating 85 from the spacer core 5. In one example, as shown in FIG. 2B, the at least one surface channel 47 is adjacent to the planar portion 48. The at least one surface channel 47 can include a plurality of surface channels 47, for example, two, three, four, five, six, up to 8 surface channels 47. In some preferred embodiments, the at least one surface channel 47 can be disposed on the outer locking surface 46 directly adjacent the planar portion 48. In particularly preferred embodiments, the planar portion 48 has two surface channels 47 directly adjacent where one surface channel 47 is directly adjacent to one side of the planar portion 48 and the second surface channel 47 is directly adjacent an opposing side of the planar portion 48.

In certain examples, and with reference to FIG. 3, the cap 60 can be formed as a solid body. In embodiments where the cap 60 is a solid body, the cap 60 will be attached to the rod 20 after the fluid cement material has been injected into the mold body 120. However, in alternate embodiments, and with reference to FIGS. 4A-4B, the cap 60 can include a plurality of fenestrations 12. The fenestrations 12 are configured to permit the flow of the fluid cement material into the mold body 120 to form the cement coating 85. The advantage of a cap 60 with fenestrations 12 is that the cap 60 can be attached to the rod 20 prior to the spacer core 5 being inserted into the mold body 120 while still providing one or more fluid pathways into the mold body 120 at the distal cap end 64 for introduction of the cement material into the mold body 120 to form the cement coating 85.

With continued reference to FIGS. 4A-B, the plurality of fenestrations 12 extend through the cap 60 from the distal cap end 64 to the proximal cap end 62. In certain embodiments, the fenestrations 12 extend in a direction generally coaxial with central axis C. In certain embodiments, the fenestrations extend in a generally linear direction. In certain examples, such as shown in FIG. 4A-B, the fenestrations 12 are evenly distributed around the cap 60; however, it should be appreciated that there can be any number of fenestrations 12 assuming any type of geometry or shape provided that they provide a fluid pathway into the mold body 120 from the distal cap end 64.

Figure 5B:
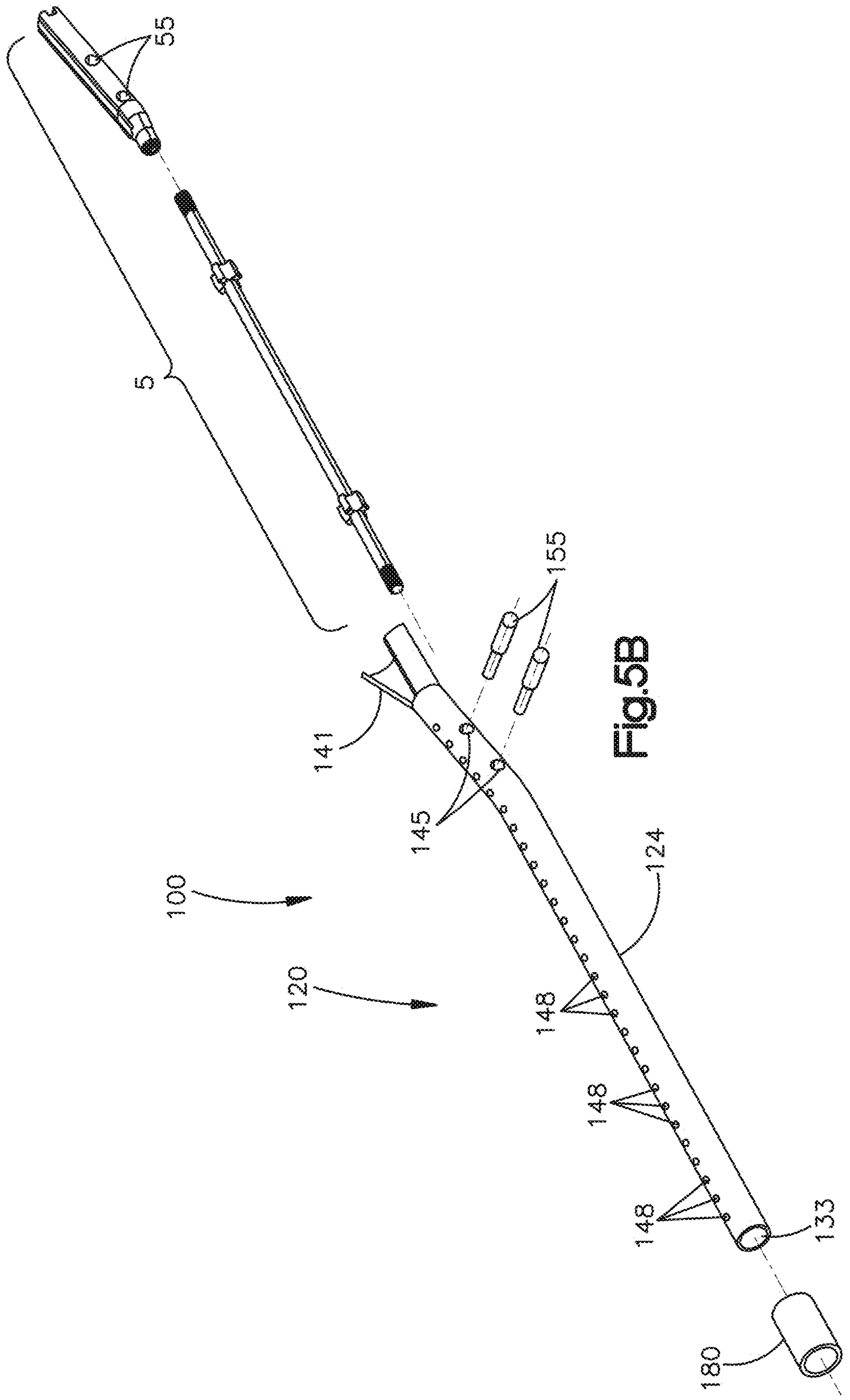
FIG. 5B is an exploded view of the mold assembly shown in FIG. 5A.

According to the present disclosure, and with reference to FIGS. 5A-B, a mold assembly 100 for forming the temporary cement spacer 1 is described including a mold body 120, the previously described spacer core 5, which is configured to be disposed within the mold body 120, at least one bore plug 155, which is configured to be disposed within the at least one locking bore 55 of the locking component 40, and an adapter 180, which is configured to operably couple the mold body 120 to a bone cement injection device that will fill the mold body 120 with the cement material that forms the cement coating 85 of the spacer core 1.

For purposes of discussion regarding the mold assembly 100, and in the interest of brevity, all of the features and embodiments, combinations and sub-combinations, previously described above with respect to the spacer core 5 (e.g., rod 20, locking component 40, cap 60, etc.) are considered to be within the scope of disclosure regarding the mold assembly 100, as well as any subsequent disclosure directed to kits, and methods of manufacture.

As previously described, the present disclosure provides a modular aspect to the manufacture of the temporary spacer 1 such that at least one benefit is providing a surgeon with the ability to customize the length of the temporary spacer 1 to match a patient anatomy. Therefore, according to certain embodiments, once the surgeon determines the appropriate length of the rod 20, and therefore the spacer core 5, the mold body 120 is configured to have its length customizable to match that desired length. As such, the mold body 120 is configured to have a portion of its length removed, if necessary, to correspond to the determined length for the temporary spacer 1. The mold body 120, in one example, can be cut to a desired length using surgical scissors or a scalpel. In certain embodiments, the mold body 120 may include interval markings or scoring corresponding to specific lengths (e.g., 1 mm intervals) to provide a visual aid for determining the desired length. Therefore, it is preferred that the mold body 120 be formed from a material that includes one or more elastomers. Suitable elastomeric materials can include, for example, silicone or polyurethane (PUR), or copolymers thereof. In certain additional embodiments, the mold body 120 comprises one or more thermoplastic materials. Suitable thermoplastic materials can include, for example, polytetrafluoroethylene (PTFE), perfluoroalkoxy alkanes (PFA), polyethylene, polypropylene, nylon, thermoplastic polyurethanes (TPU), or copolymers thereof.

With respect to the following disclosure of the mold body 120, for the purpose of convenience and ease of describing directional relationships and locations of, or along, the mold body 120, all references will be in relation to the previously identified directional identifiers used for the temporary spacer 1 and the spacer core 5. This is primarily because the mold assembly 100 includes the spacer core 5 disposed within the mold body 120. Therefore, for example, the use of terms such as "axial," "radial," "proximal," "distal," "longitudinal," and any derivations thereof are intended to be consistent between the previously defined temporary spacer 1 and spacer core 5, and the mold assembly 100 and the mold body 120 that will be further described. For example, as will be described below, a central axis C of the mold body 120 is intended to be at the same as previously described with respect to the temporary spacer 1 and the spacer core 5. Accordingly, the mold assembly 100 includes a mold body 120 that is elongate in the same longitudinal direction L as the rod 20 such that the central axis C defined by the rod 20 likewise defines the central axis C of the mold body 120. The mold body 120 further defines a proximal mold end 121 and a distal mold end 123 opposite the proximal mold end 121 along the central axis C and an outer mold surface 124 extending therebetween.

The mold body 120 additionally defines a proximal mold opening 131 at the proximal mold end 121 and a distal mold opening 133 at the distal mold end 123 and an inner mold surface 138 extending therebetween. The inner mold surface 138 defines a mold lumen 136. The mold lumen 136 is configured to have the spacer 5 disposed within it. In other words, the mold assembly 100 includes the spacer core 5 disposed within the mold lumen 136, for example as shown in FIG. 5A.

With continuing reference to FIGS. 5A-5B, the mold assembly 100 further includes at least one bore plug 155 configured to be disposed within the at least one locking bore 55 of the locking component 40. The function of the at least one bore plug 155 is to fill the at least one locking bore 55. Because the locking bores 55 are configured to receive one or more locking screws that will secure the temporary spacer 1 to bone, the function of at least one bore plug 155 is to prevent any cement material from becoming lodged in the locking bores 55 during the injection of the cement material into the mold body 120 during formation of the cement coating 85. The at least one bore plug 155 can be inserted into the at least one locking bore 55 prior to any injection of cement material into the mold body 120, and once the temporary spacer 1 has been formed, the at least one bore plug 155 is configured to be removed from the at least one locking bore 55.

In certain examples, the spacer core 5 can include more locking bores 55 than will be utilized by locking screws during implantation. As was previously described, the locking component 40 of the spacer core 5 can include multiple locking bores 55 to provide a surgeon with multiple options for utilizing a locking screw, or multiple locking screws, to secure the temporary spacer 1 to the adjacent bone. Thus, a surgeon, or other medical professional, can determine prior to the formation of the temporary spacer 1, which, or how many, of the locking bores 55 will be designated to receive a locking screw, and therefore utilize the corresponding number of bore plugs 155 to fill those designated locking bores 55. Accordingly, those locking bores 55 not designated to receive a bore plug 155 can be left open and cement material could therefore fill the unused radial bores 55. This could be advantageous in further strengthening the attachment of the cement coating 85 to the spacer core 5. Thus, it can be said that a first portion of a the plurality of locking bores 55 contain a bore plug 155 disposed within them, and a second portion of the locking bores 55 are open, or do not contain a bore plug 155 disposed within them.

Alternatively, a surgeon or other medical professional may not be able to determine which, or how many, of the locking bores 55 they will need to utilize for receiving locking screws until they contemporaneously evaluate the anatomical conditions at the implant site. In such examples, in order to preserve the availability of each of the locking bores 55 for locking screws, each of the locking bores 55 can be filled with bore plugs 155.

With continuing reference to FIGS. 5A-5B, the mold body 120 can include at least one mold bore 145 that is configured to receive a bore plug 155. The at least one mold bore 145 is also configured to align with at least one of the locking bores 55 when the spacer core 5 is disposed within the mold body 120. The at least one mold bore 145 extends radially with respect to the central axis C through the mold lumen 136. As previously noted, directional modifiers used with respect to the mold body 120 are to be understood to be used consistently with respect to the spacer core 5 such that the use of the terms “radial” or “radially” or derivations thereof are directions or locations defined with respect to the central axis C and can include radially inward direction towards the central axis C as well as radially outward direction away from the central axis C. In certain examples, the radial direction R is oriented perpendicular to the central axis C and in other examples the radial direction R can be angularly offset from a direction that is perpendicular to the central axis C but is not coaxial or parallel with the central axis C.

The function of the at least one mold bore 145 is to allow the at least one bore plug 155 to be inserted into the at least one locking bore 55 when the spacer core 5 is disposed within the mold body 120, and further to permit the removal of the at least one bore plug 155 from the at least one locking bore 55, after the formation of the temporary spacer 1 (i.e., after the cement material has been injected into the mold body 120 and the cement coating 85 has been formed) while the temporary spacer 1 is still disposed within the mold body 120. One benefit to having the bore plug 155 be configured to fit in both the at least one locking bore 55 of the spacer core 5 and the at least one mold bore 145 of the mold body 120 is that such a mold assembly 100 can act as a self-aligning feature. In other words, when the spacer core 5 is disposed within the mold body 120, the mold body 120 and the spacer core 5 can be considered properly oriented and aligned with respect to each other when the mold bores 145 and the locking bores 55 of the spacer core 5 are in alignment with one another, and are a capable of receiving a bore plug 155, as can be seen, for example in FIG. 5A. Accordingly, it can be said that in certain examples of the mold assembly 100, the at least one bore plug 155 is disposed within and extends through both the at least one locking bore 55 and the at least one mold bore 145.

In certain embodiments, the number of mold bores 145 is the same as the number of locking bores 55. In alternative embodiments, the number of mold bores 145 is less than the number of locking bores 55. As previously described, the spacer core 5 can include a number of locking bores 55 that will exceed the actual number of locking screws that will be utilized by the surgeon. Thus, in certain embodiments, the mold body 120 may be constructed to include a smaller number of mold bores 145 than the corresponding number of locking bores 55 formed in the spacer core 5. For example, in embodiments where there are a plurality of locking bores 55, there may be certain locking bore 55 positions in the spacer core 5 that have a higher percentage, or likelihood, of being utilized in a surgical procedure, and certain locking bore 55 locations of the spacer core 5 with a lower percentage of being used. Therefore, the mold body 120 can include, on the one hand, the same exact number of mold bores 145 as the locking bores 55 of the spacer core 5, or alternatively can have less. The potential benefit to having less is that it can minimize the number of locations where the cement material could potentially leak out from along the mold body 120, which could potentially compromise the integrity of the resulting cement coating 85.

According to certain embodiments, the at least one bore plug 155 can comprise a plurality of bore plugs 155, such as, for example, two, three, four, five, six, or even up to eight bore plugs 155. For instance, as shown in FIGS. 5A-5B, there are two radial bore plugs 155 configured to fit within each of the two mold bore 145 and the corresponding two locking bores 55 of the spacer core 5.

With continued reference to FIGS. 5A-5B, as well as FIGS. 9A-9D and 10A-10B, the mold assembly 100 can further include an adapter 180 configured to operably couple the mold body 120 to a cement injection device 210 so as to provide a continuous fluid pathway from the cement injection device 210 into the mold lumen 136 where the spacer core 5 is disposed for the cement material to form the cement coating 85 on the spacer core 5, and thus form the temporary spacer 1. While the following description of the adapter 180 and the accompanying figures describe the adapter 180 operably coupled to the distal mold end 123 of the mold body 120, it should be appreciated that the adapter 180 can be coupled to the proximal mold end 121 of the mold body 120 as well.

Figure 10A:
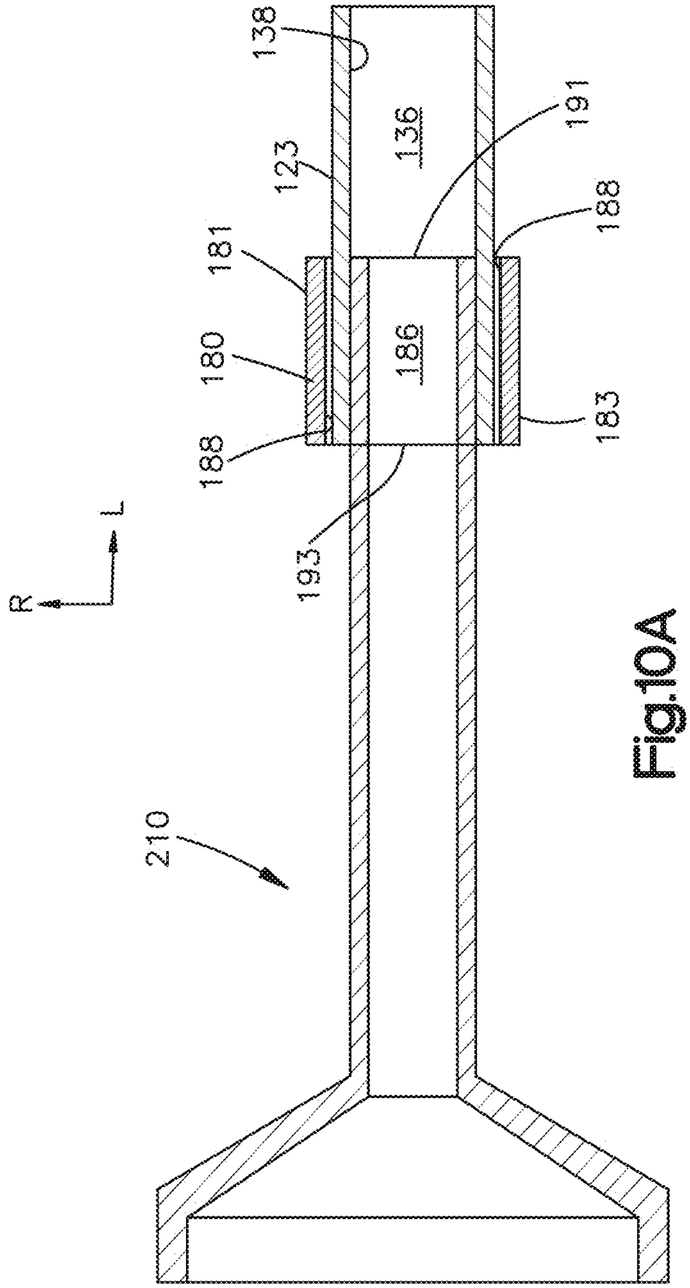
FIG. 10A is a cross section side view of an alternate embodiment of an adapter, bone cement injection device, and distal end of mold body according to certain embodiments.
Figure 10B:
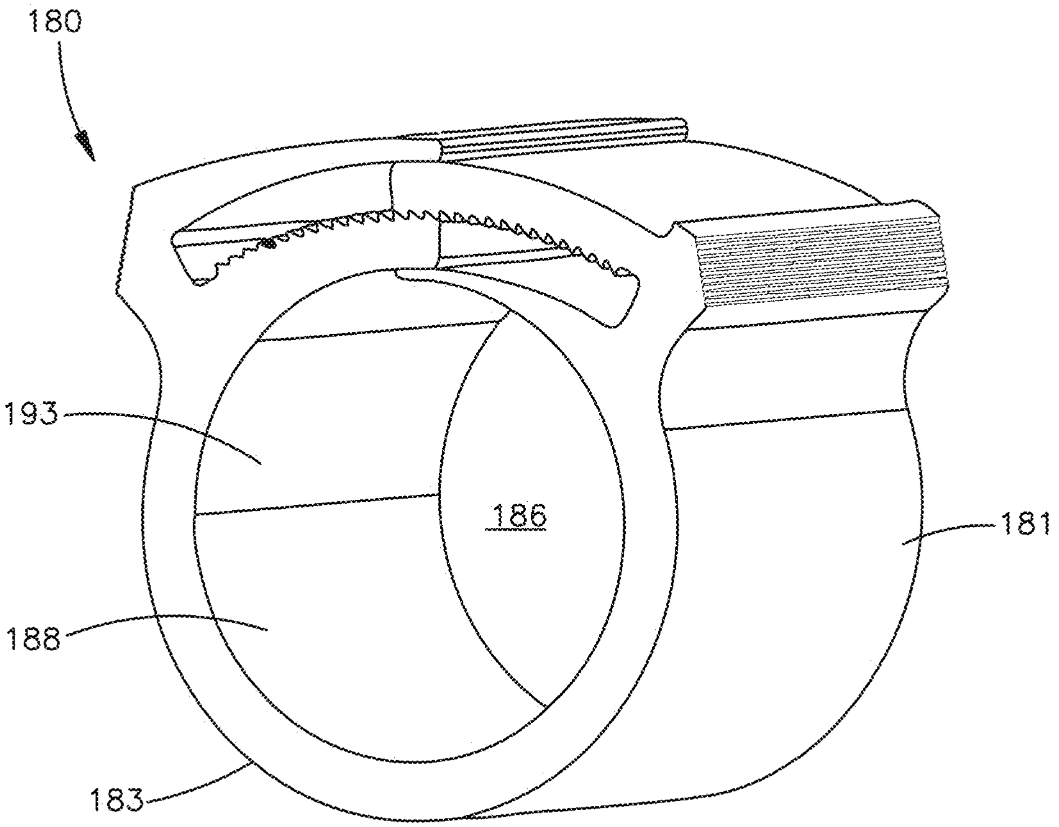
FIG. 10B is a perspective view of the distal end of the adapter shown in FIG. 10A.

As shown, the adapter 180, when coupled to the distal mold end 123, extends from the mold body 120 along the longitudinal direction L such that the adapter 180 is aligned with the mold body 120 along the central axis C. The adapter 180 defines a proximal adapter end 181 that is configured to couple to the distal mold end 123, and a distal adapter end 183, opposite the proximal adapter end 181 along the central axis C. As shown, the distal adapter end 183 is configured to operably couple to the cement injection device 210. Additionally, the adapter 180 further defines a distal adapter opening 193 at the distal adapter end 183, and an adapter inner wall 188 that extends from the distal adapter opening 193 towards the proximal adapter end 181. The adapter inner wall 188 defines an adapter recess 186. Adapter recess 186 provides a continuous fluid pathway from the cement injection device 210 into the mold body lumen 136. According to certain embodiments such as shown in FIGS. 9A-9D, the adapter inner wall 188 can be threaded such that operably coupling the adapter 180 to the cement injection device 210 comprises threadingly coupling the adapter 180 with the cement injection device 210. Alternatively, such as shown in FIG. 10A-10B, the adapter 180 can include a clamp in order to securely couple cement injection device 210 to the distal mold end 123.

With continued to reference to FIGS. 9A-9D, the inner wall 188 can further include an adapter receptacle 195 disposed within the adapter recess 186 and extending proximally towards the mold body 120. The adapter receptacle 195 can have a receptacle opening 196 facing the proximal adapter end 181. In certain embodiments, the distal rod end 24 can be configured to engage with and be disposed within the receptacle opening 196. The function of the receptacle opening 196 is, when the distal rod end 24 is seated within the receptacle opening 196, to properly center the rod 20 within the mold body to better permit the formation of a uniform cement coating 85 along the rod outer surface 26. According to certain embodiments, the adapter receptacle 195 can have an inner threaded surface and the distal rod end 24 can be threadingly engaged in the adapter receptacle 195.

With reference to FIGS. 5-8, in certain instances the mold body 120 includes separation means extending generally along the central axis C from the proximal mold end 121 to the distal mold end 123 that are configured to separate the mold body 120. The function of the separation means is to split or otherwise separate the mold body 120 so as to provide a way for the temporary spacer 1 to be freed from the mold body 120 without damage after the cement coating 85 has cured.

Figure 6:
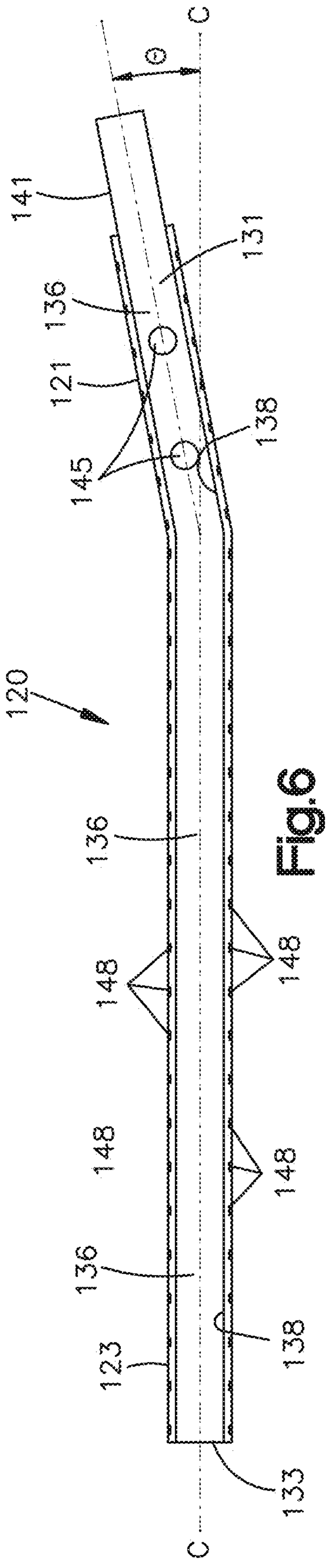
FIG. 6 is a cross-section side view of a mold body according to certain embodiments showing a plurality of perforations extending axially along the mold body.

In certain embodiments, and with reference to FIGS. 5A-B and 6, the separation means comprises a plurality of perforations 148 arranged in a row extending in an axial direction along the mold body 120 from the proximal mold end 121 towards the distal mold end 123. In certain embodiments, there can be multiple rows of the plurality of perforations 148 along the mold body 120, for example, as shown in the embodiment depicted in FIG. 6, two separate rows of perforations 148 can extend axially along the mold body 120 between the proximal mold end 121 and the distal mold end 123.

Figure 7:
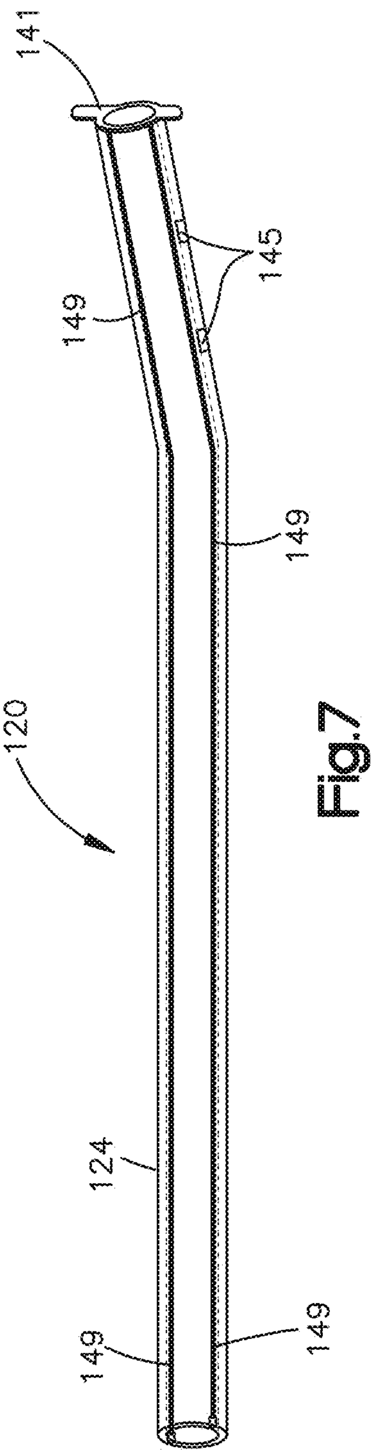
FIG. 7 is a perspective view of an alternate embodiment of the mold body according to certain embodiments showing two strips of material embedded in the mold body and extending axially.

Alternatively, and with reference to FIG. 7, separation means can include at least one strip of material 149 extending axially and disposed within the mold body 120 between the outer mold surface 124 and the inner mold surface 138. For examples, as shown in FIG. 7, there are two strips of material 149 that extend axially between the proximal mold end 121 and distal mold end 123.

Figure 8A:
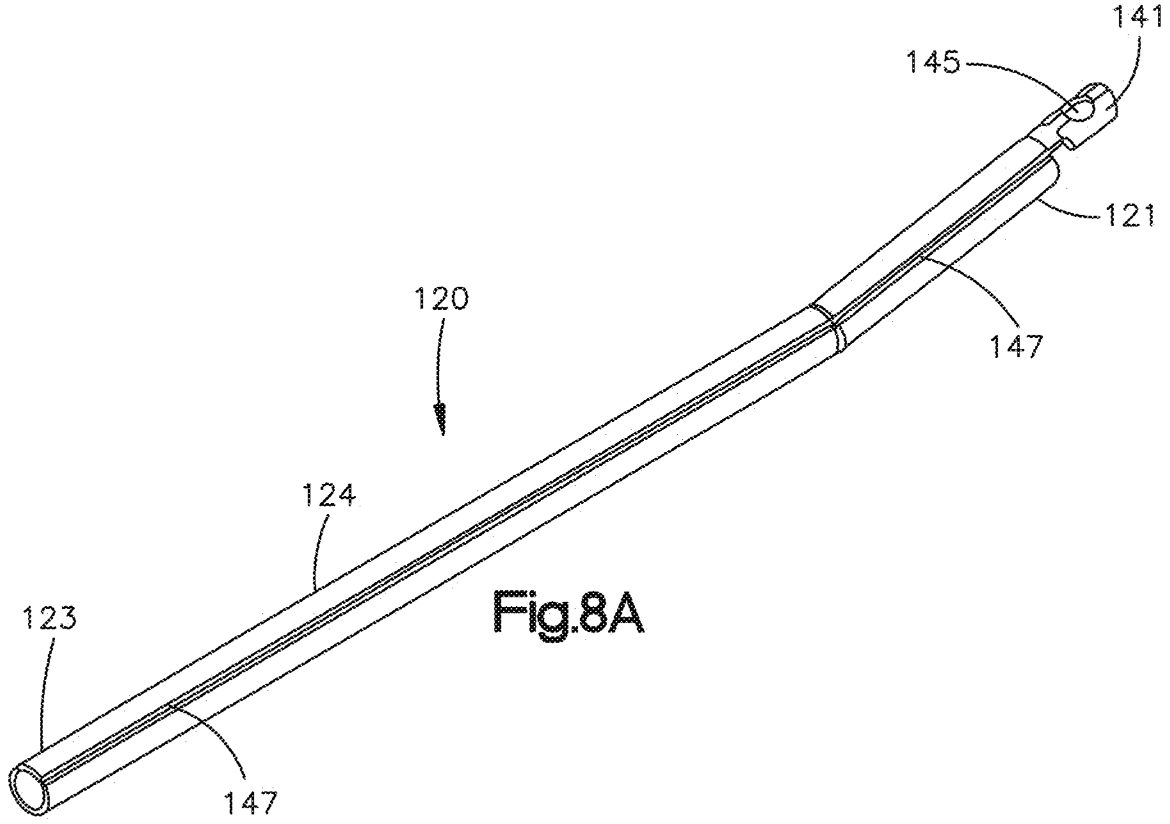
FIG. 8A is a perspective view of another alternate embodiment of the mold body showing a pair of axially extending grooves along the outer surface of the mold body.
Figures 8B, 8C, 8D:
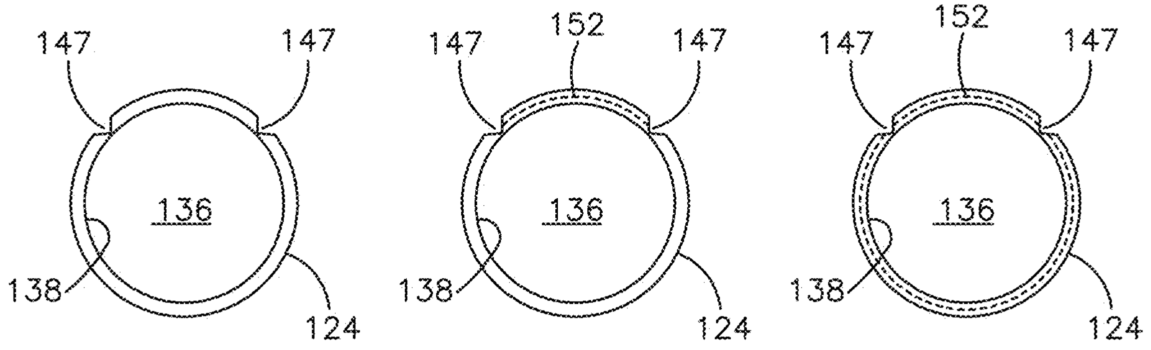
FIG. 8B is a cross-sectional view of the mold body shown in FIG. 8A.
FIGS. 8C-D are cross-section views of an alternative mold body of the one shown in FIG. 8A-B, showing reinforcement of the mold body.
Figure 9A:
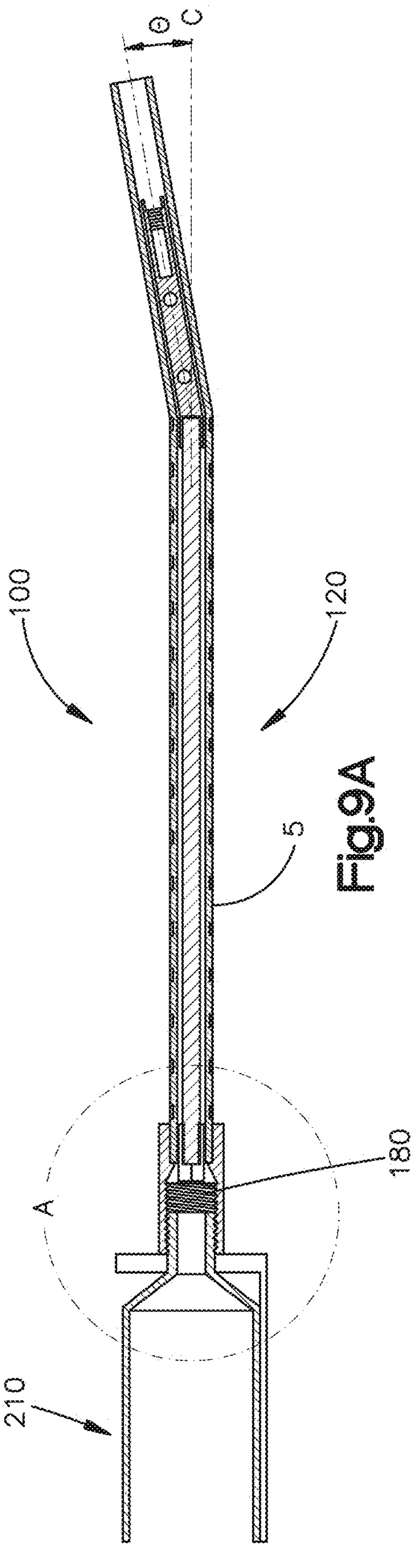
FIG. 9A is a cross-section side view of the mold assembly of FIG. 5A coupled to a bone cement injection device with an adapter.
Figure 9B:
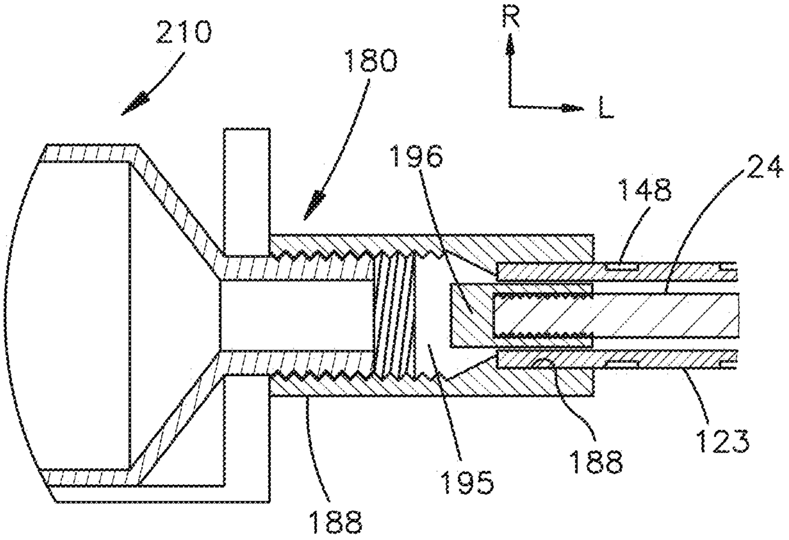
FIG. 9B is an enlarged view of the area within circle A of FIG. 9A.
Figure 9C:
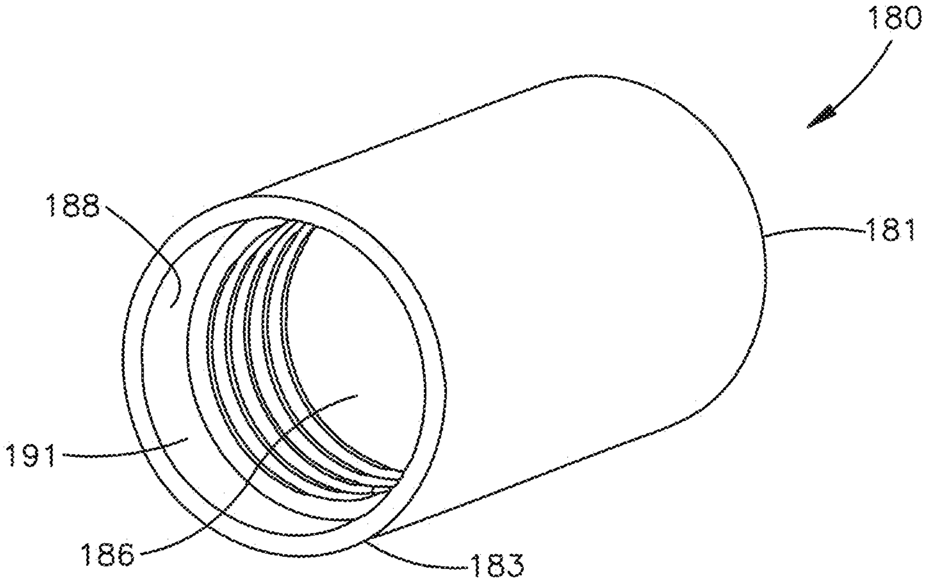
FIG. 9C is a perspective view of the distal end of the adapter of FIG. 9A.
Figure 9D:
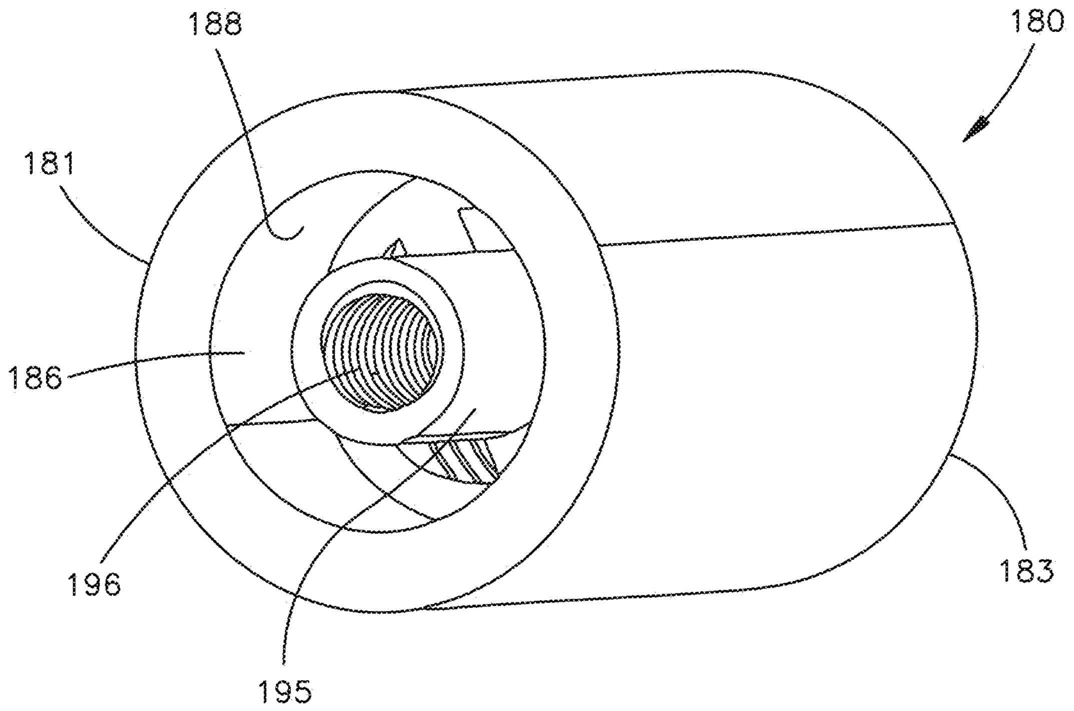
FIG. 9D is a perspective view of the proximal end of the adapter of FIG. 9A.

In a further alternative embodiment, as shown in FIGS. 8A-8D, the mold body 120 can include a groove 147, or a plurality of grooves 147, such as two grooves 147, formed in the outer mold surface 124, extending axially along the length of the mold body 120 from the proximal mold end 121 towards the distal mold end 123. With reference to FIGS. 8C-D, the mold body 120 can additionally include one or more reinforcing members 152 disposed within mold body 120, which in combination with the grooves 147, are configured to permit the controlled directed separation of the mold body 120 along grooves 147. In other words, the inclusion of the reinforcing members 152 in the mold body 120 direct the separation of the mold body along the path of the grooves 147, so as to reduce the possibility of the mold body 120 tearing in an unintended direction.

With continued reference to FIGS. 5-8, the mold body 120 can further include one or more tabs 141 disposed at either the proximal mold end 121 or the distal mold end 123. The one or more tabs 141 are configured to be grasped, for example manually or mechanically, and pulled in order to initiate the separation of the mold body 120 along the direction of the separation means. For example, a user can grasp the one or more tabs 141 and pull, thus applying a force that will cause the separation means to separate the mold body 120 along the defined separation means. For example, when the mold body 120 includes perforations 148, as shown in FIGS. 5A-5B and 6, or groove 147, as shown in FIG. 8, pulling the one or more tabs 141 will apply a force to the mold body 120 along the row of perforations 148 or the grooves 147 causing the mold body 120 to split along the separation means. When the mold body 120 includes strips of material 149, as shown in FIG. 7, a user can pull the tabs 141 causing the strips 149 to slice the mold body 120 along the line of the strips 149.

As previously described, in certain embodiments, the locking component 40 can be offset with respect to the direction of the central axis C by an angle theta, θ. In embodiments where the locking component 40 is offset, the proximal mold end 121 (where the locking component 40 is disposed in the mold assembly 100) can be likewise offset from the central axis C by the same angle theta θ (see. e.g. FIG. 9A).

According to the present disclosure, a kit for forming the temporary cement spacer 1 is disclosed. The kit can include a mold body 120, at least one adapter 180, a locking component 40, at least one bore plug 155, at least one rod 20, and a cap 60. It should be appreciated that each of the disclosed components can be provided in the kit as a separate component. Alternatively, each of the disclosed kit components can be provided in the kit already connected with a corresponding component or multiple components in a manner consistent with what has been previously described. For example, the rod 20, the locking component 40, and the cap 60 have already been described as elements of the spacer core 5 configured to be connected. As such, any combination of the these three components can be provided in the kit already connected, such that the kit can be provided including the rod 20 connected to the locking component 40, the rod 20 connected to the cap 60, or the rod 20 connected to both the locking component 40 and the cap 60. As another example, the kit can be provided with a separate mold body 120 and adapter 180, or alternatively, the adapter 80 can be provided connected to the mold body 120.

In certain examples, the kit can be provided where the at least one rod 20 can include a plurality of rods 20, such as, for example, two, three, four, five, six, seven, eight, nine, or ten rods 20. In a preferred embodiment, each rod 20 of the plurality of rods 20 has a length, measured between the proximal rod end and the distal rod end, and each rod length of the plurality of rods 20 is different than any other rod length of the plurality of rods 20. In other words, the kit is provided with multiple rods 20 of differing lengths. As previously disclosed, in one respect, the temporary spacers 1 of the present disclosure are configured to be modular with respect to their length and the ability of the surgeon to determine and customize the spacer core 5 length. Thus, by providing a plurality of rods 20, where each of the rods 20 has a different length, a surgeon is able to customize the spacer core 5 to have the desired length that most closely approximates the patient's anatomical dimensions.

Alternatively, as previously described, the rod 20 can include an outer surface 26 that comprises a substantially, or even entirely, threaded surface 28. In such instances, the kit can include a single rod 20 that includes a continuously threaded surface 28 and a surgeon can determine the appropriate length for the rod 20 and cut the rod 20 to the desired length.

The kit can further include at least one locking bone screw, for example the kit can include a plurality of locking screws, such as two, three, four, five, six, seven, or eight locking screws that are configured to be disposed in the locking bore 55 and secure the temporary spacer 1 to bone.

With reference to FIG. 11, the kit can include an insertion instrument 300 configured to operably couple to the locking component 40. As shown in FIG. 11, insertion instrument 300 is operably coupled to the proximal locking end 42 through the placement of insertion screw 303 into proximal locking recess 53.

The present disclosure additionally describes a method of forming an antimicrobial eluting temporary cement spacer. The method can include the steps of:

inserting a spacer core into a lumen of a mold body, the spacer core including a rod and a locking component connected to the rod, wherein the locking component includes at least one locking bore;

coupling a bone cement injection device to the mold body with an adapter to provide a fluid pathway from the bone cement injection device into the mold body lumen;

disposing at least one bore plug into the at least one locking bore;

injecting bone cement material including one or more antimicrobial agents into the mold body lumen through the fluid pathway along at least a portion of an outer surface of the rod;

curing the bone cement material on the outer rod surface so as to form a cement coating, whereby the antimicrobial eluting temporary cement spacer is formed;

decoupling the bone cement injection device from the mold body;

removing the at least one bore plug from the at least one locking bore; and, separating the mold body from the antimicrobial eluting temporary cement spacer.

The method can further include, prior to the step of inserting the spacer core 5 into the mold lumen 136, connecting the rod 20 to the locking component 40, such as for example, operably coupling the proximal rod end 22 to the distal locking end 44 as previously described.

As previously described the rod 20 has a rod length, and the method can further include, removing a portion of the length of the rod 20 from either the proximal rod end 22 or the distal rod end 24. In a preferred embodiment, after the step of removal, the length of the spacer core 5 is less than or equal to a length of the mold body 120. Additionally, and as previously described, the mold body 120 has a length, and the method can further include removing a portion of the length of the mold body 120 from either the proximal mold end 122 or the distal mold end 124.

According to additional embodiments, the mold body 120 comprises at least one mold bore 145, and the step of inserting the spacer core 5 into the mold lumen 136 can further include aligning the at least one mold bore 145 with the at least one locking bore 55. Additionally, the step of disposing at least one bore plug 155 into the at least one locking bore 55 can further include disposing the at least one bore plug 155 into the at least one mold bore 145 and the at least one locking bore 55. In certain further embodiments, where the at least one locking bore 55 includes a plurality of locking bores 55, the method includes disposing a plurality of bore plugs 155 into each locking bore 55 of the plurality of locking bores 55. Alternatively, where the at least one locking bore 55 includes a plurality of locking bores, the method can include inserting at least one bore plug 155 into the plurality of locking bores 55 such that at least one locking bore 55 of the plurality of locking bores 55 does not receive a bore plug 155. In embodiments where at least one locking bore 55 does not receive a bore plug 155, the step of injecting the bone cement material can include filling the at least one locking bore 55 that did not receive a bore plug 155 with the bone cement material. In still further embodiments, where the at least one mold body bore 145 includes a plurality of mold bores 145, the method includes disposing the plurality of bore plugs 155 into each mold bore 145 of the plurality of mold bores 145.

As previously described, in certain embodiments, the cap 60 is configured to be attached to the distal rod end 24 such that in such instances the spacer core 5 can be said to include the rod 20, the locking component 40, and the cap 60. As such, the methods can further include the step of attaching a cap 60 to a distal rod end 24 of the rod 5. Further, as described, where the distal rod end 24 includes a threaded surface 28, the step can include threading the cap 60 onto the threaded surface 28 of the distal rod end 24. As previously described, the cap 60 can include a plurality of fenestrations 12 extending through the cap 60. As such, where the cap 60 includes fenestrations 12, the step of attaching the cap 60 to the rod 20 can occur at any time prior to the step of injecting the bone cement material, as well as, after the step of decoupling the bone cement injection 210 device from the mold body 120. Thus, where the cap 60 includes fenestrations 12, the step of injecting bone cement material can include injecting bone cement material through the fenestrations 12.

Figure 12:
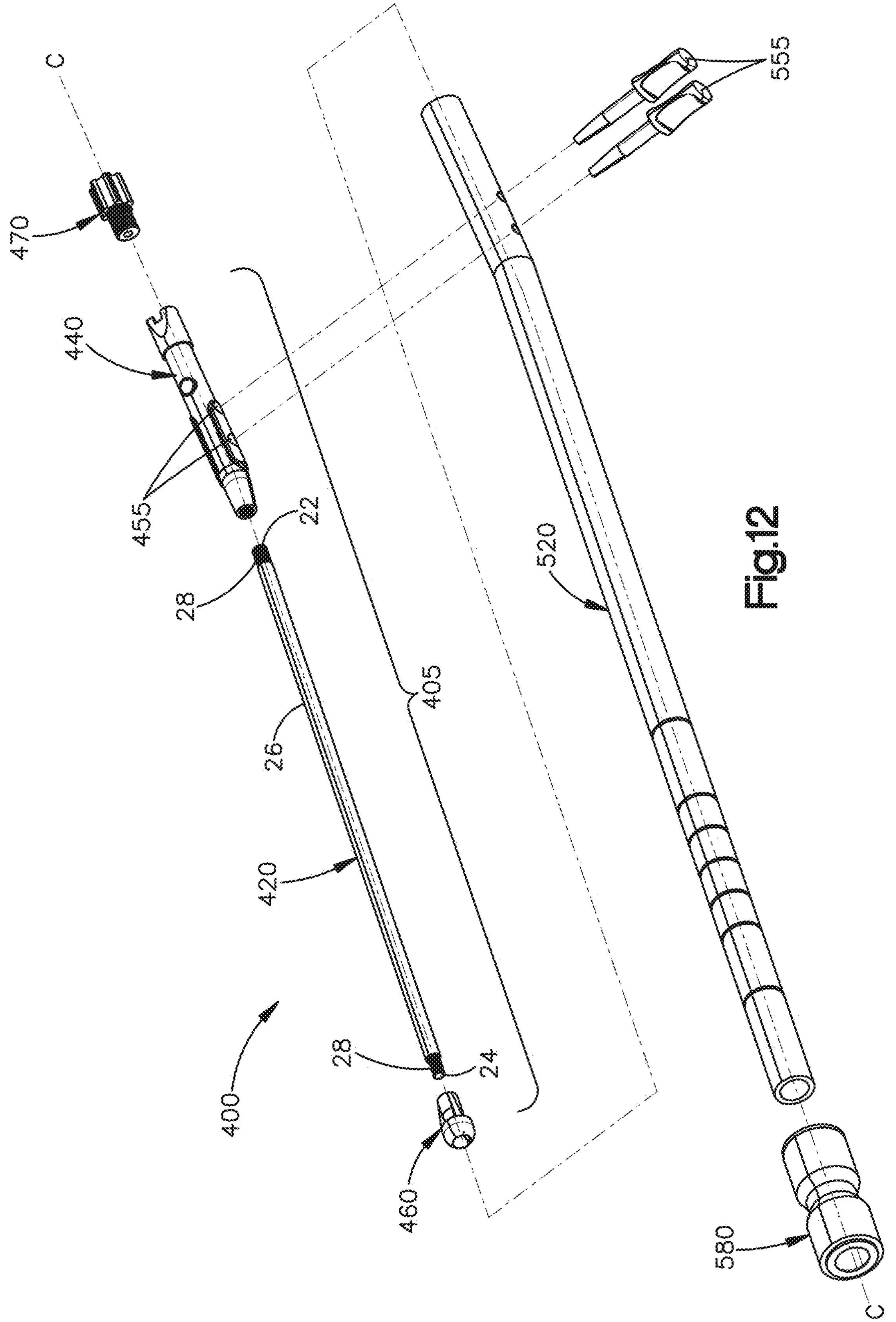
FIG. 12 is a perspective exploded view of a mold assembly according to additional embodiments of the present disclosure.

Referring now to FIG. 12, an additional embodiment of a mold assembly 400 for forming a temporary cement spacer 1 is described. The mold assembly 400 includes a mold body 520 and a temporary spacer core 405 configured to be disposed within the mold body 520. The spacer core 405 is configured to provide the structural framework of the temporary spacer 1, and includes a rod 420, a locking component 440, and a cap 460. The mold assembly includes at least one bore plug 555 configured to be disposed within the at least one locking bore 455 of a locking component 440. The mold assembly 400 also includes an adapter 580 configured to operably couple the mold body 520 to a bone cement injection device that will fill the mold body 520 with the cement material that forms a cement coating 485 of the spacer core 1. The mold assembly 400 can also include a proximal plug member 470 configured to couple with the proximal end of the locking component.

For purposes of discussion regarding the mold assembly 400, and in the interest of brevity, all of the features and embodiments, combinations and sub-combinations, described above with respect to the spacer core 5 (e.g., rod 20, locking component 40, cap 60, etc.) are considered to be within the scope of disclosure regarding the mold assembly 400, as well as any subsequent disclosure directed to kits, and methods of manufacture. The following disclosure will focus on differences between the mold assembly 400, and components thereof, relative to the mold assemblies and components described above with reference to FIGS. 1A-11.

The rod 420 is configured similar to the rod 20 described above. The rod 420 defines a proximal rod end 22, a distal rod end 24 opposite the proximal rod end 22 along the central axis C, and an outer rod surface 26 extending from the proximal rod end 22 to the distal rod end 24. The proximal rod end 22 is configured to attach to the locking component 440. For example, a portion of the outer rod surface 26 at the proximal rod end 22 can define a locking feature, such as a threaded surface 28, that can lock with a complimentary locking feature, such as an inner distal locking surface 33, of the locking component 440. The distal rod end 24 is configured to attach to the cap 460. For example, a portion of the outer rod surface 26 at the distal rod end 24 can define a locking feature, such as a threaded surface 28, that can lock with a complimentary locking feature, such as a threaded inn cap surface 71, of the cap 60. In the present embodiment, the rod outer surface 26 is preferably smooth and devoid of protrusions between the threaded surfaces 28 at the proximal and distal rod ends 22, 24. For example, the rod outer surface 26 of the present embodiment can be devoid of centering members, such as the centering members 31 described above.

Referring now to FIGS. 13A-13D, the locking component 440 is configured similar to the locking components 40 described above. Accordingly, the locking component 440 can include the various associated features described above, including, for example, the proximal locking end 42, proximal locking opening 50, proximal locking inner surface 51, proximal locking recess 53, distal locking end 44, distal locking opening 32, inner distal locking surface 33, distal locking recess 35, outer locking surface 46, one or more locking bores 55, and offset angle θ.

One difference in the present embodiment, however, is that the outer locking surface 46 can define one or more projections 49, which can define radially outward portions of the one or more locking bores 55. The one or more projections 49 can also be referred to as "bosses" or "islands," and can each define an outer projection surface 451 that is spaced outward from a main recessed surface portion 449 of the outer locking surface 46 by a distance R1 measured along the radial direction R. The one or more projections 49 can beneficially increase the gap or void volume between the mold body 520 and the locking component 440 when the spacer core 405 is disposed within the mold body 520. This increased gap or void volume provides additional space along the outer locking surface 46 to receive and be occupied by cement material injected into the mold body 520 for forming the cement coating 85.

In the illustrated embodiment, the one or more projections 49 can include a first pair of radially opposed projections 49*a* along at least a first locking bore 55*a* and a second pair of radially opposed projections 49*b* along at least a second locking bore 55*b*. It should be appreciated that each projection 49 can extend along a single locking bore 55 or along a plurality of locking bores 55. Additionally or alternatively, the one or more projections 49 can extend along other features, such as along the proximal locking end 42. For example, the one or more projections 49 can include a proximal mounting projection 49*c* configured to couple with a complimentary geometry of an instrument, such as the insertion instrument 300. The proximal mounting projection 49*c* can define one or more surface channels 447, which can be configured to vent gas (e.g., air) as the cement 85 progresses through the mold. The one or more surface channels 447 can also beneficially provide a visual indication of when the mold has been filled (or at least substantially filled) with cement 85, and can additionally provide a simplified "clean up" feature through which excess cement 85 can be extruded and discarded from the mold. As shown, the proximal mounting projection 49*c* can define a single surface channel 447 that has a dovetail cross-sectional profile, which can be configured to retain the cement 85 therein after curing. Alternatively, the surface channel 447 can have other profile shapes, such as a U-shaped cross-sectional profile or a V-shaped cross-sectional profile, by way of non-limiting examples. It should be appreciated that the proximal locking end 42 is preferably configured to selectively mount to a plurality of instruments, such as various insertion instruments 300 (e.g., various aiming arms and the like). In this manner, the spacer core 405 can be mountable to various types of surgical instruments based on patient needs.

The one or more projections 49 can also define retention structures for interfacing with the injected cement after hardening for enhancing stability of the interface between the cement coating 85 and the locking component 440. Such retention structures can include inwardly tapered surfaces or "notches" along one or more various sides and/or ends of the projection 49. For example, one or both of the first pair of radially opposed projections 49*a* can include tapered side surfaces 453 that taper inwardly towards each other as they extend radially inward toward the central axis C. Additionally or alternatively, one or both of the second pair of radially opposed projections 49*b* can include tapered side surfaces 457 that taper inwardly towards each other as they extend radially inward toward the central axis C. These tapered side surfaces 457 can also define channels which, similar to the channels 47 described above, can receive portions of the cement coating 85 and provide shielding from the mechanical forces that occur during implantation and explanation. Additionally, the tapered side surfaces 453, 457 can cause the respective outer projection surfaces 451 to radially overhang respective portions of the main recessed surface portion 449, which can facilitate retention of the cement coating 85 along the locking component 440, particularly during exposure to forces acting on the cement coating 85 during implantation or explanation (e.g. torsion) that could cause fracture or delamination of the cement coating 85 from the locking component 440. It should be appreciated that other retention structure geometries can be employed along the one or more projections 49.

Figure 13A:
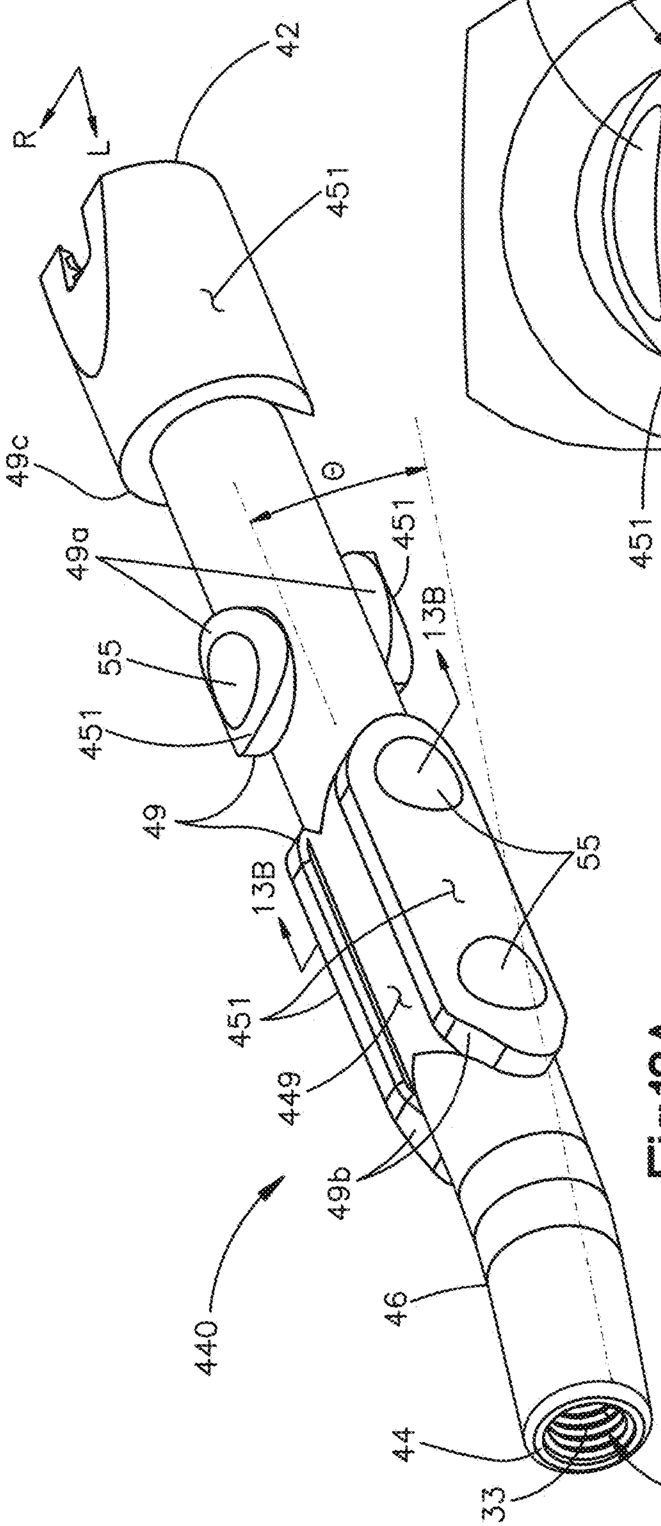
FIG. 13A is a perspective view of a locking component of the mold assembly shown in FIG. 12.
Figure 13B:
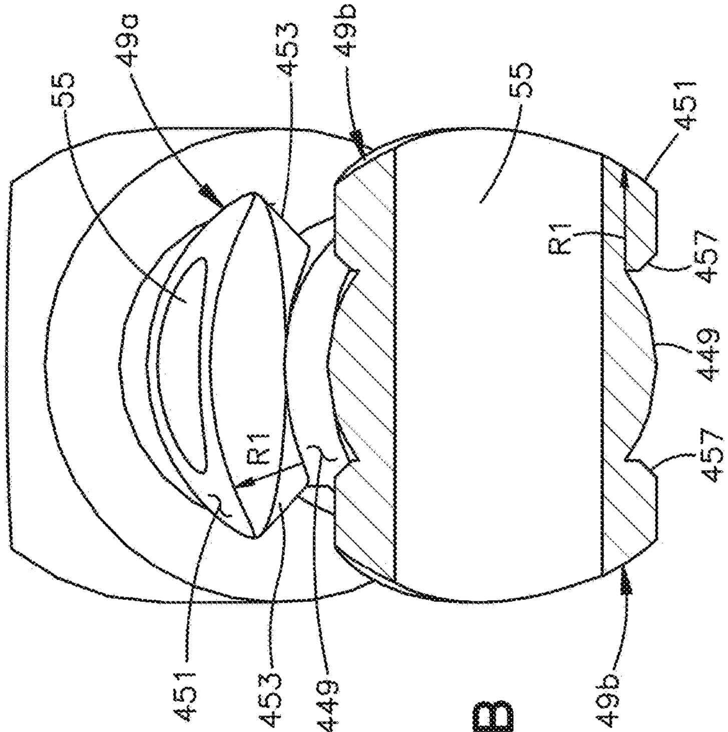
FIG. 13B is a cross-sectional end view of the locking component taken along section line 13B-12B in FIG. 13A.
Figure 13C:
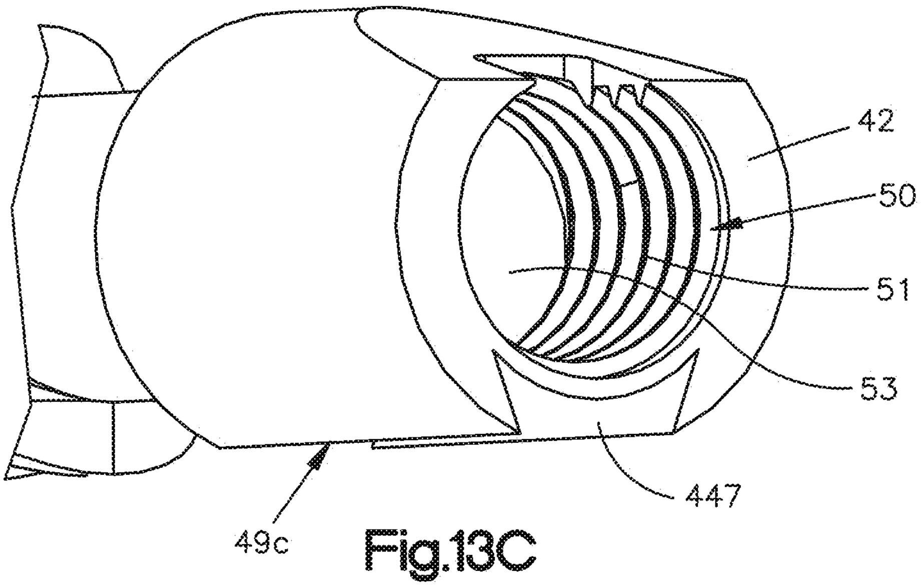
FIG. 13C is a perspective view of a proximal end of the locking component shown in FIG. 13A.
Figure 13D:
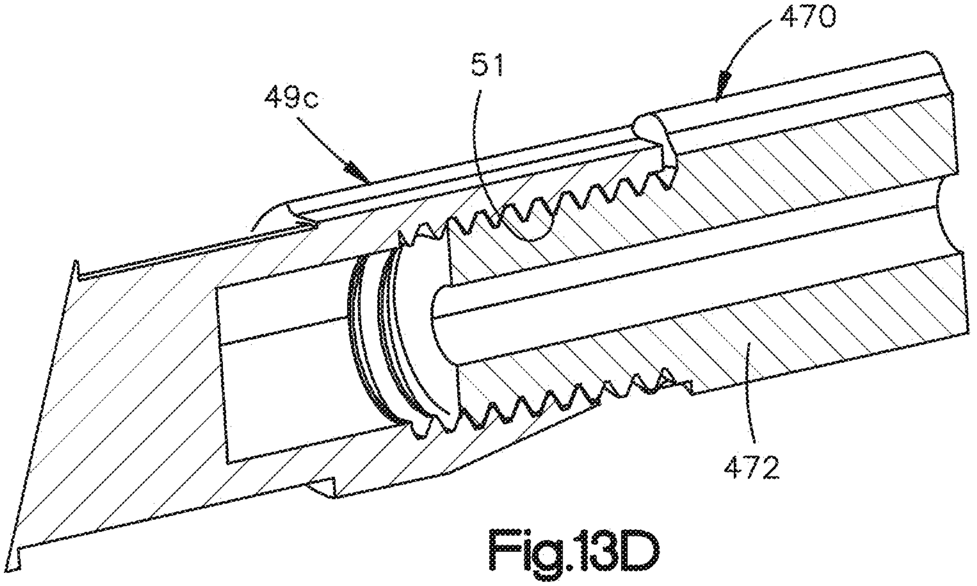
FIG. 13D is a cross-section perspective view of the proximal end of the locking component shown in FIG. 13A having an end plug coupled therewith according to additional embodiments of the present disclosure.

As shown in FIG. 13D, the proximal plug member 470 can be configured to temporarily couple with the proximal locking inner surface 51 of the locking component 440. The proximal plug member 470 can include a distal insertion portion 472 for insertion within the proximal locking recess 53. Preferably, the distal insertion portion 472 is externally threaded for threadingly engaging the internal threads of the proximal locking inner surface 51. In this manner, the proximal plug member 470 can occlude and prevent flow of cement 85 into the proximal locking opening 50 during the cement injection process. Accordingly, the proximal plug member 470 can also be referred to as a "thread protector" for the proximal locking end 42 of the locking component 440.

Figure 14A:
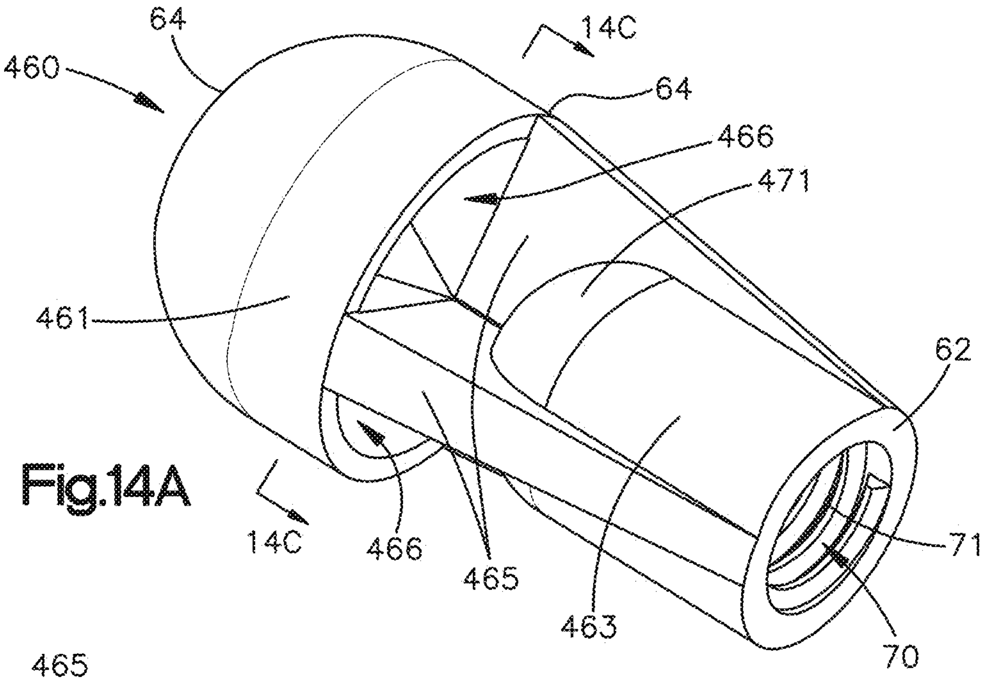
FIG. 14A is a perspective view of a cap of the mold assembly shown in FIG. 12.
Figure 14B:
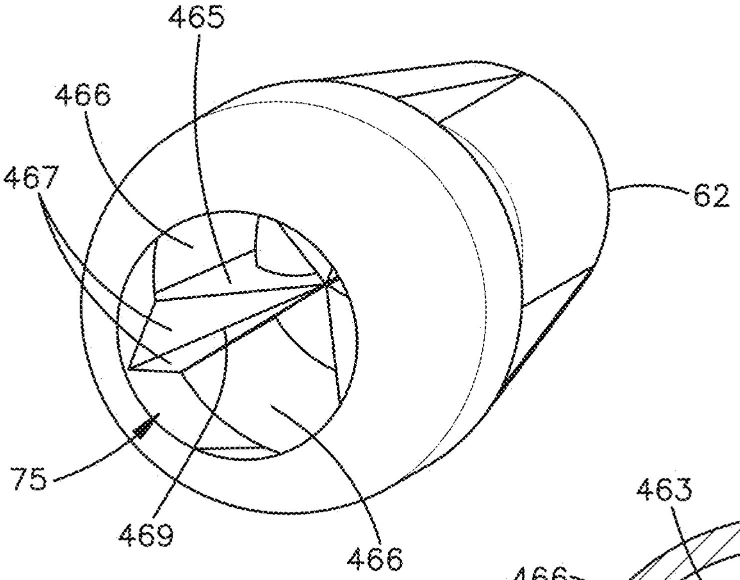
FIG. 14B is another perspective view of the cap shown in FIG. 14A, illustrating cement channels defined by the cap.
Figure 14C:
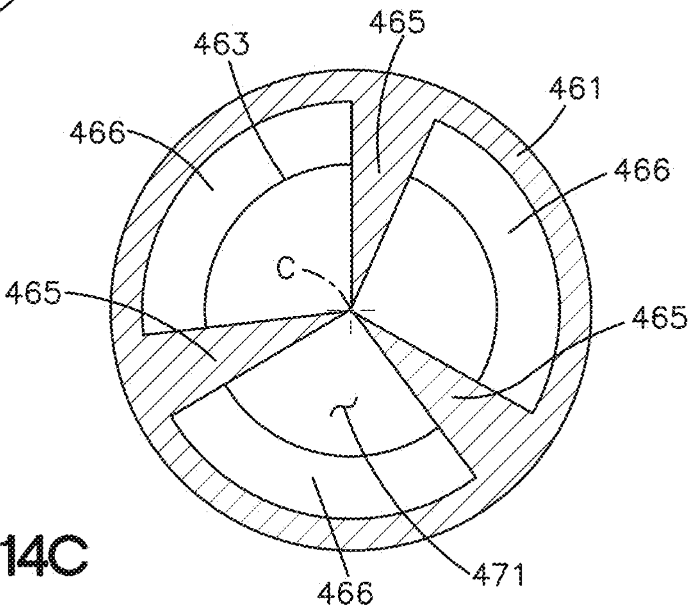
FIG. 14C is a cross-section end view of the cap taken along section line 14C-14C in FIG. 14A.

Referring now to FIGS. 14A-14C, the cap 460 is configured similar to the caps 60 described above. Accordingly, the cap 460 can include the various associated features described above, including, for example, the proximal cap end 62, proximal cap opening 70, inner cap surface 71, cap recess 73, distal cap end 64, and outer cap surface 66. In the present embodiment, however, instead of fenestrations 12, the cap 460 can include a distal cap opening 75, which is preferably centrally arranged with respect to the central axis C. The distal cap end 64 is defined by a distal cap portion 461 that is connected to a proximal hub portion 463 by a plurality of arms 465, which are circumferentially spaced from each other about the central axis C. In this manner, the cap 460 defines openings or channels 466 that are located circumferentially between the arms 465 and are in fluid communication with the distal cap opening 75 so as to facilitate the flow of cement 85 therethrough. One advantage of a cap 460 configured in this manner is that the channels 466 can be wider and can present less contact surface area along the cap 460 body than fenestrations, such as the fenestrations 12 described above, and can thus provide less resistance to the cement 85 during injection thereof. The proximal hub portion 463 can define the proximal cap end 62, the cap opening 70, the inner cap surface 71, and the cap recess 73, which can be configured as described above.

As shown, the cap 460 can have three (3) arms, which are preferably evenly spaced from each other circumferentially (i.e., at 120 degree intervals) about the central axis C. It should be appreciated that in other embodiments the cap 640 can have one (1), two (2), four (4), five (5), or more than five arms 465, which can be evenly or unevenly spaced from each other. As shown, the arms 465 preferably define distal surfaces 467 that taper to leading edges 469 for reducing resistance (e.g., drag) to cement 85 being injected through the distal cap opening 75. The leading edges 469 of the arms 463 can also taper radially inwardly and distally from the distal cap portion 461 to the proximal hub portion 463. A distal surface 471 of the proximal hub portion 463 can be rounded or otherwise configured to facilitate flow of cement 85 through the cap 460.

The cap 460 can define a maximum cap cross-sectional area that is similar to the maximum cross-sectional area of the temporary spacer 1. For example, the maximum cap cross-sectional area can be in a range of 70 percent to 100 percent of the maximum cross-sectional area of the temporary spacer 1, or more particularly in a range of 85 percent to 95 percent of the maximum cross-sectional area of the temporary spacer 1, or preferably in a range of about 88 percent to about 92 percent of the maximum cross-sectional area of the temporary spacer 1. It should be appreciated that for the foregoing example ranges, the maximum cross-sectional area of the temporary spacer 1 can be defined by the locking component 440.

Figure 15A:
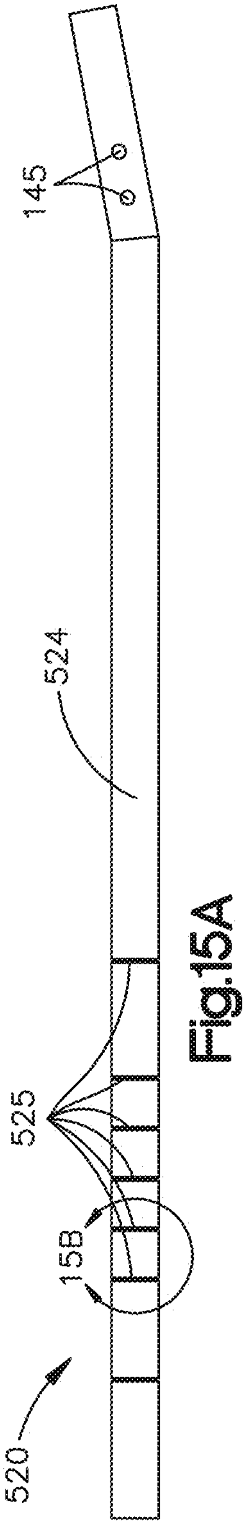
FIG. 15A is a side view of a mold body of the mold assembly shown in FIG. 12.
Figure 15B:
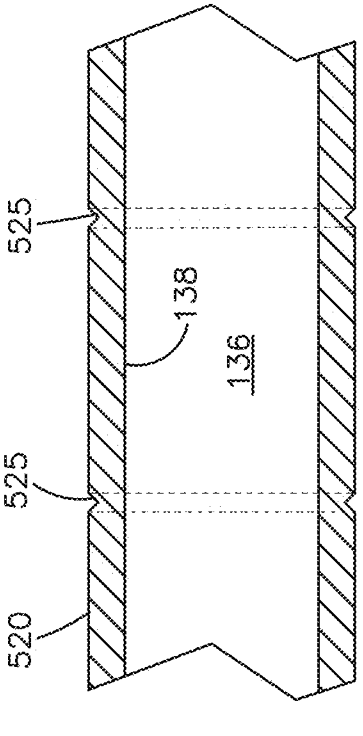
FIG. 15B is a cross-section side view a portion of the mold body within circle 15B of FIG. 15A.

Referring now to FIGS. 15A-15C, the mold body 520 is configured similar to the mold bodies 120 described above for forming a temporary spacer 1. Accordingly, the mold body 520 can include the various associated features described above, including, for example, the proximal mold end 121, proximal mold opening 131, outer mold surface 124, distal mold end 123, distal mold opening 133, mold lumen 136, mold inner surface 138, and one or more mold bores 545, for example. Similar to the mold body 120 described above, the mold body 520 of the present embodiment is configured to have its length customizable to match the desired length of the spacer core 405. Accordingly, the mold body 520 preferably includes visual indicia, such as a series of markings 525 spaced at intervals corresponding to specific lengths (e.g., 1-mm intervals) to provide a visual aid for determining the desired length. The markings 525 can be drawn, painted, etched, anodized, and/or scored on the mold outer surface 524. Preferably, the mold body 520 is also formed of a material that is translucent or at least semi-translucent, thereby allowing a surgeon or other qualified medical professional to view the spacer core 405 and/or cement disposed inside the mold body 520 during the formation process. It should be appreciated that, based on the length of the selected rod 420, the distal cap end 64 preferably substantially aligns with one of the markings 525 when the spacer core 405 is placed alongside the mold body 520. Thus, the surgeon can visually reference the distal cap end 64 alongside the mold body 520 to identify the desired customized length of the mold body 520. Moreover, the surgeon can optionally designate one of the visual markings as the desired location to cut the mold body 520. The mold body 520 preferably defines weakened portions, such as scoring, along the markings 525 to facilitate or otherwise direct the cut to occur at the select marking 525.

Figures 16A, 16B, 16C:
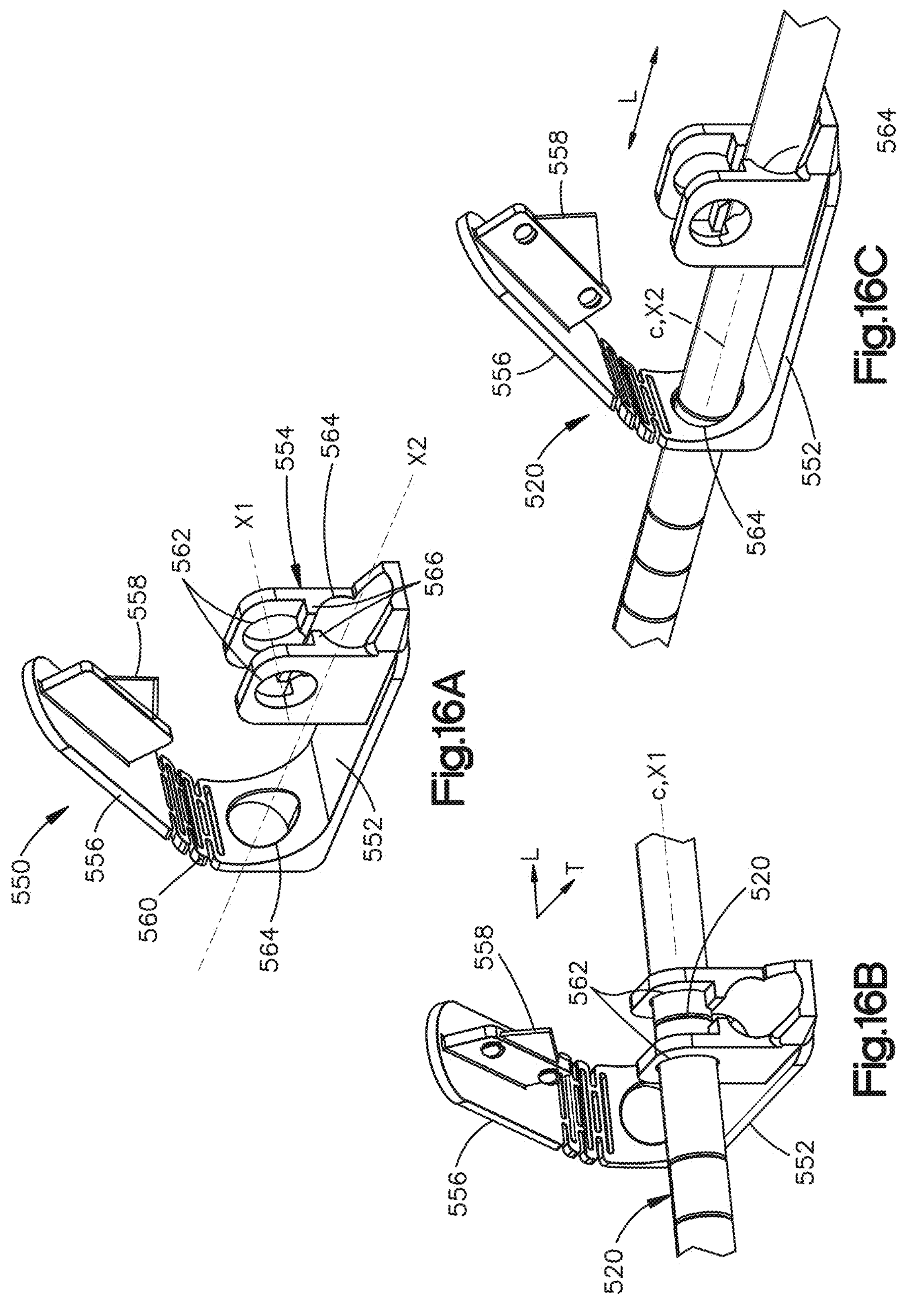
FIG. 16A is a perspective view of a cutting tool for cutting the mold body shown in FIG. 15A.
FIG. 16B is another perspective view of the cutting tool shown in FIG. 16A, illustrating the cutting tool oriented to perform a transverse cut of the mold body.
FIG. 16C is another perspective view of the cutting tool shown in FIG. 16A, illustrating the cutting tool oriented to perform a longitudinal slice along a length of the mold body.

Referring now to FIGS. 16A-16C, the mold body 520 is configured to be cut to the desired length using a cutting device, such as a multi-function cutting device or "cutter" 550 of the mold assembly 400. It should be appreciated that the mold body 520 is also configured to facilitate being cut to the desired length using other cutting devices, such as surgical scissors or a scalpel, by way of non-limiting examples. The multi-function cutter 550 of the present embodiment includes a first support member 552 that has a guide formation 554 for removably coupling with the mold body 520 for multi-function cutting (e.g., selective multi-directional cutting), as described in more detail below. The cutter 550 includes a second support member 556 that carries a cutting member, such as a blade 558, and is pivotably connected to the first support member 552 via a hinge structure 560. In the present embodiment, the hinge structure 560 is a compliant (i.e., flexible) member, which can be defined by a plurality of voids or apertures configured to induce bending along the hinge structure 560. The hinge structure 560 can be monolithic with both the first and second support members 552, 556, as shown.

The guide formation 554 can be configured to multi-directional cutting by defining first and second mounting formations for performing first and second respective cuts along first and second respective cutting directions. For example, the first mounting formation can be a first pair of slots 562 aligned along a first guide axis X1, which is configured to be substantially coaxial with the central axis C when the mold body 520 extends through the first pair of slots 562, thereby aligning the blade 558 (and thus the first cutting direction) along a transverse direction T that is substantially perpendicular to the longitudinal direction L. In this manner, the mold body 520 can be inserted through the first pair of slots 562 for cutting the mold body 520 to the desired length. The guide formation 554 can also include a reference formation, such as one or more visualization projections 566 defining a gap therebetween, which can be configured for providing the surgeon with a visual reference of the cutting path of the blade 558. In this manner, when performing the length-determining cut of the mold body 520, the surgeon can use the reference formation 566 to align the cutting path with the desired marking 525. The second mounting formation can be a second pair of slots 564 aligned along a second guide axis X2, which is configured to be substantially coaxial with the central axis C when the mold body 520 extends through the second pair of slots 564, thereby aligning the blade 558 (and thus the second cutting direction) along the longitudinal direction L. In this manner, the mold body 520 can be inserted through the second pair of slots 564 for cutting (e.g., slicing) the mold body 520 longitudinally along its length to decouple the mold body 520 from the temporary spacer 1 after the cement coating 85 has cured.

Figure 17:
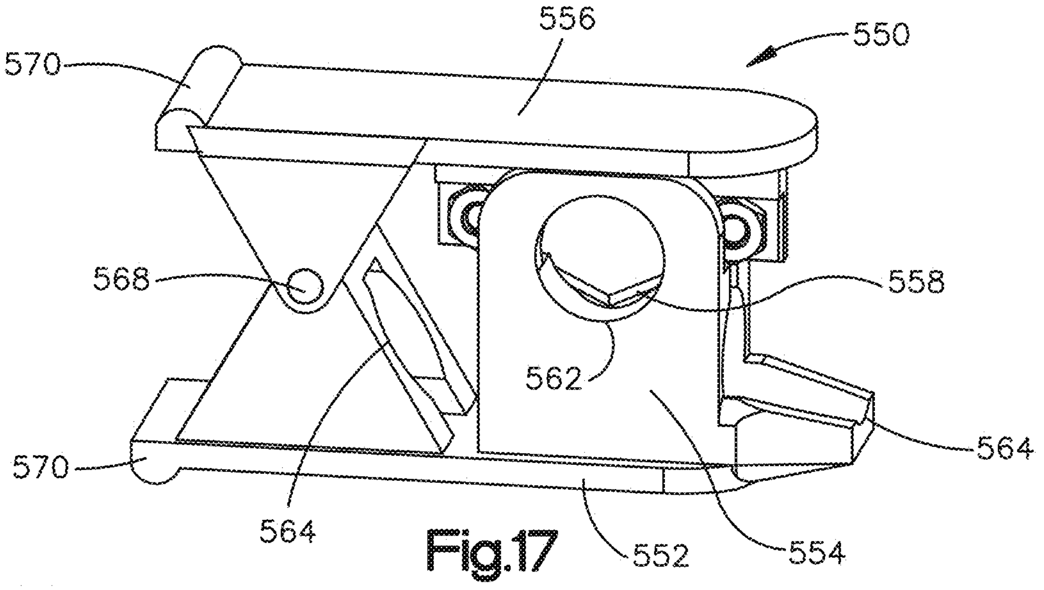
FIG. 17 is a perspective view of an another embodiment of a cutting tool for cutting the mold body shown in FIG. 15A.

Referring now to FIG. 17, in another embodiment of the cutter 550, the hinge structure 560 can employ a pivot pin 568 that pivotably joins the first and second support members 552, 556. In this embodiment, proximal ends 570 of the first and second support members 552, 556 can be pressed toward each other about the pivot pin 568, which acts as a fulcrum, to open the cutter 550 for insertion of the mold body 520 through one of the first or second pairs of slots 562, 564. The cutter 550 of this embodiment can otherwise be configured similarly to the cutter 550 described above with reference to FIGS. 16A-16C.

Figure 18A:
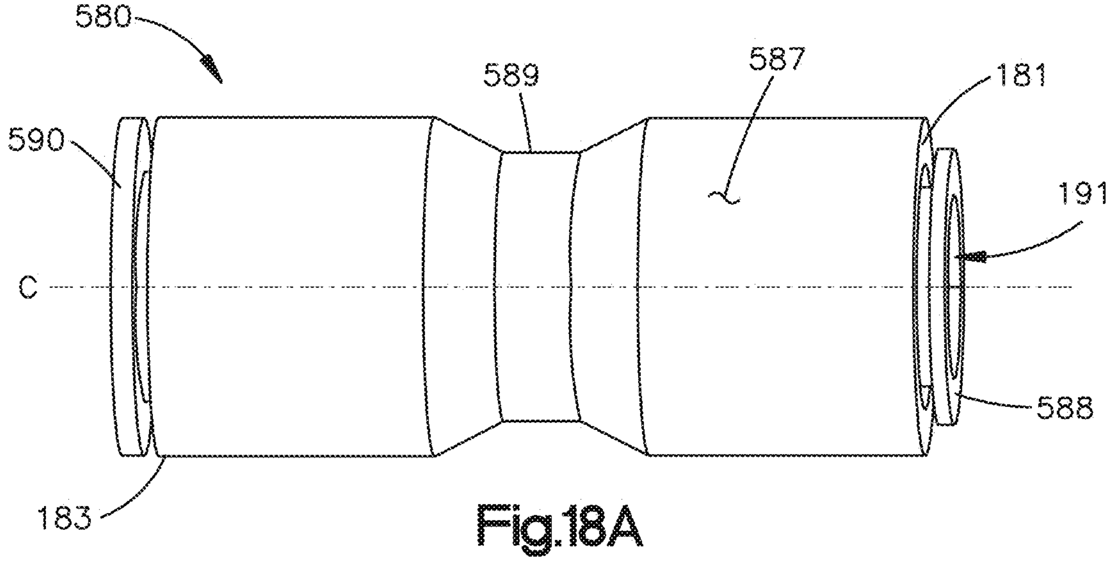
FIG. 18A is a perspective view of an adapter of the mold assembly shown in FIG. 12.
Figure 18B:
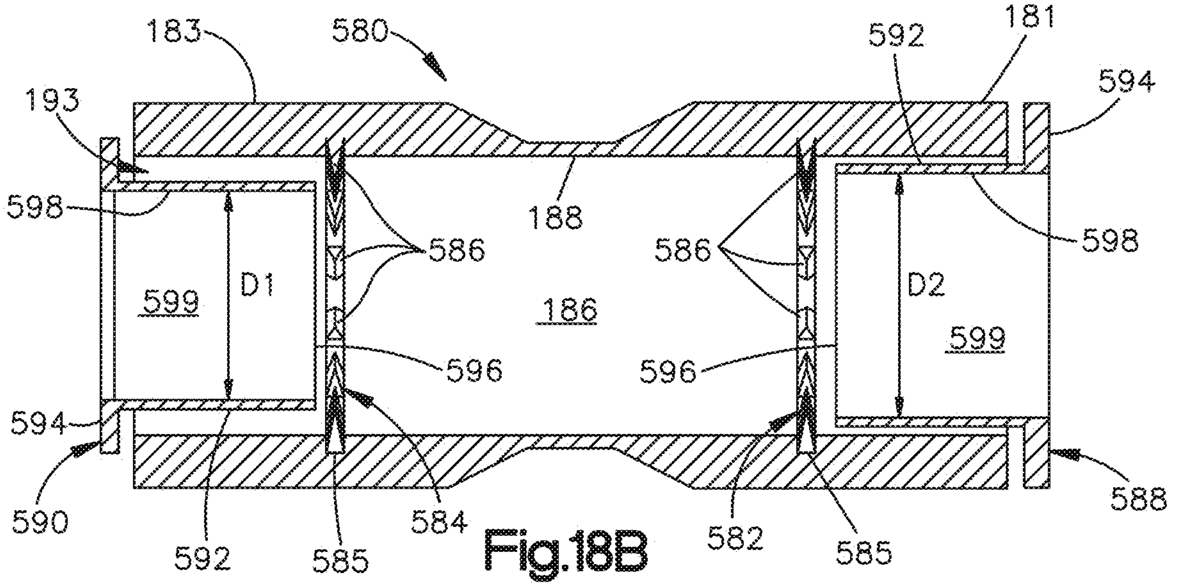
FIG. 18B is a cross-section side view of the adapter shown in FIG. 18A.
Figure 18C:
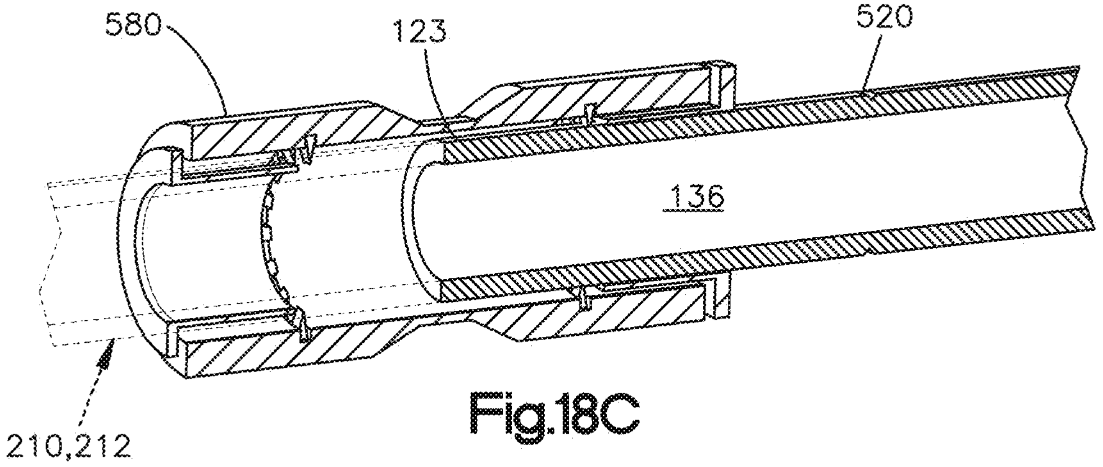
FIG. 18C is a cross-section perspective view of the adapter shown in FIG. 18A coupled to the mold body shown in FIG. 15A.

Referring now to FIGS. 18A-18C, the adapter 580 is configured generally similar to the adapters 180 described above for operably coupling the mold body 520 to a component of a cement injection device 210, such as an injection tube 212 of an injection syringe 210. Accordingly, the adapter 580 includes various features of the adapters described above, including a proximal adapter end 181 that is configured to couple to the distal mold end 123, and a distal adapter end 183, opposite the proximal adapter end 181 along the central axis C. As described above, the distal adapter end 183 is configured to operably couple to the injection tube 212. Additionally, the adapter 580 further defines a proximal adapter opening 191 at the proximal adapter end 181, a distal adapter opening 193 at the distal adapter end 183, and an adapter inner wall 188 that extends from the proximal adapter opening 191 to the distal adapter opening 193. The adapter inner wall 188 defines an adapter lumen 186 that provides a continuous fluid pathway from the injection tube 212 into the mold body lumen 136. The adapter 580 also defines an adapter outer surface 587, which can define a mounting formation, such as an exterior recess 589, which can extend annularly around a circumference or a partial circumference of the adapter 580.

In the present embodiment, as shown in FIG. 18B, the adapter 580 can include one or more internal retention features, such as first and second retention features 582, 584, that are configured to securely grip the mold body 520 and the cement injection device 210, respectively, when they are fully inserted or "seated" within the adapter lumen 186. For example, the first and second retention features 582, 584 can each be an annular retention ring having a plurality of fingers or teeth 586 extending radially inwardly toward the central axis C. The retention rings 582, 584 can reside within respective annular recesses 585 within the adapter inner wall 188. The teeth 586 can have geometries configured to non-destructively grip the respective outer surfaces of the mold body 520 and the injection tube 212. For example, the teeth 586 can be formed of a flexible material, which can grip the mold body 520 and the injection tube 212, respectively, with sufficient retention force to "hold" the mold body 520 and injection tube 212 is position with the adapter lumen 186 during the cement injection process, but also such that the mold body 520 and injection tube 212 can be subsequently non-destructively decoupled from the teeth 586.

Preferably, the adapter 580 also includes one or more release members, such as a first release member 588 for releasing the mold body 520 from the adapter 580 and a second release member 590 for releasing the injection tube 212 from the adapter 580. One or both of the first and second release members 588, 590 can include a tubular insertion body 592 and an actuator, such as an actuation flange 594 extending radially outwardly from the tubular insertion body 592. The first and second release members 588, 590 are shown in FIG. 18B in respective neutral positions. The release member 588, 590 can be selectively actuated to a release position by pressing the respective actuation flange 594 in a manner forcing the tubular insertion body 592 further into the adapter lumen 186, causing an inner end 596 of the tubular insertion body 592 to press against the teeth 586 of the respective retention ring 582, 584. In this manner, when in the release position, the tubular insertion body 592 can deflect the teeth 586 out of engagement with the mold body 520 or injection tube 212, respectively, thereby allowing the surgeon to retract the respective mold body 520 or injection tube 212 from the adapter 580 as needed.

Preferably, the tubular insertion bodies 592 define interior surfaces 598 that define respective lumens 599 that are sized to snugly receive one but not both of the mold body 520 and the injection tube 212. For example, the interior surface 598 of the first release member 588 can define an inner diameter D1 that is substantially equivalent to an outer diameter of the distal mold end 123, so that the distal mold end 123 can be snugly received within the lumen 599 of the first release member 588. The foregoing diameters can be greater than an inner diameter D2 of the interior surface 598 of the second release member 590, which can in turn be substantially equivalent to an outer diameter of the injection tube 212, so that the injection tube 212 can be snugly received within the lumen 599 of the second release member 590. In this manner, the distal mold end 123 would not fit within the lumen 599 of the second release member 590, thus ensuring that the distal mold end 123 gets inserted within the proper end of the adapter 580 (i.e., the proximal adapter end 181). Thus, once the distal mold end 123 is inserted within the adapter 580, the injection tube 212 can only be inserted within its associated end of the adapter 580 (i.e., the distal adapter end 183). It should be appreciated that, in other embodiments, the injection tube 212 can have an outer diameter that is greater than that of the distal mold end 123. In yet other embodiments, the injection tube 212 and the distal mold end 123 can have substantially equivalent outer diameters D1, D2, and each can fit snugly in the lumens 599 of both release members 588, 590.

It should be appreciated that the distal adapter end 183 is preferably configured to couple with standard-type injection syringes, which provides significant benefits, such as the ability to use adapter 580 for injection with a large number of various injection devices that employ such standard-type injection syringes.

Figure 19A:
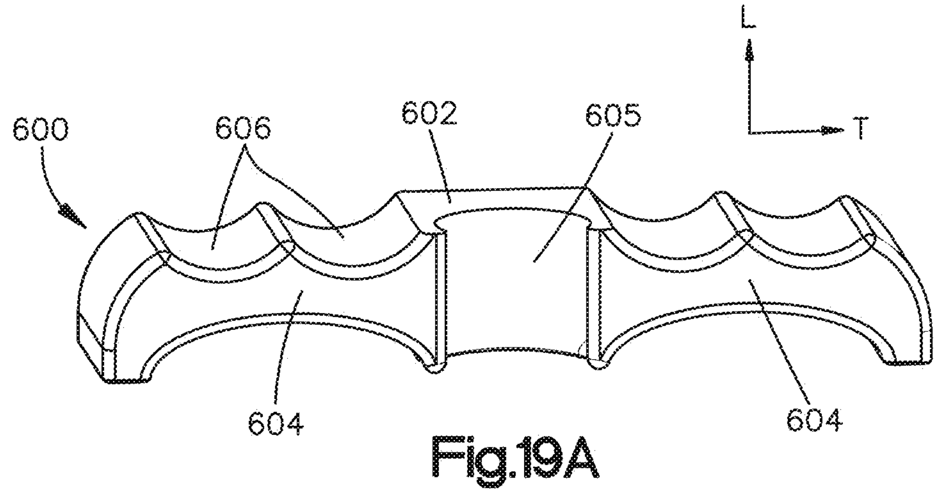
FIG. 19A is a perspective view of a handle member for use with the adapter shown in FIG. 18A.
Figure 19B:
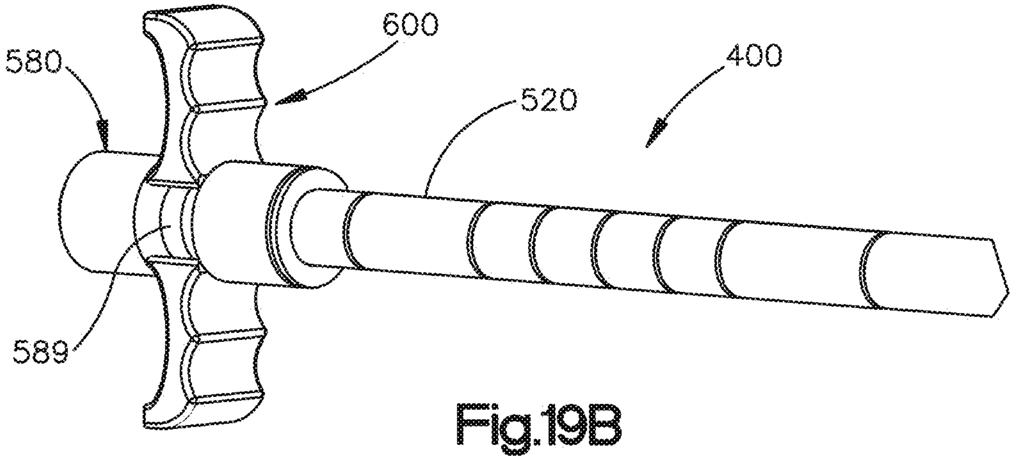
FIG. 19B is a perspective view of the handle member shown in FIG. 19A coupled to the adapter shown in FIG. 18C.

Referring now to FIGS. 19A-19B, the mold assembly 400 can include a grip or "handle" member 600, such as for use with the adapter 580 to provide the surgeon with a grip support during the cement injection process. The handle member 600 can include a central mount 602 and a pair of extensions 604 extending oppositely therefrom along the transverse direction T. The central mount 602 can define a slot 605 for engaging a complimentary structure of the adapter 580, such as the exterior recess 589. The extensions 604 can include grip formations 606, such as scallops configured to provide finger holds, which can provide gripping support for the surgeon's fingers to effectively grasp the adapter 580 during the cement injection process.

Figure 20A:
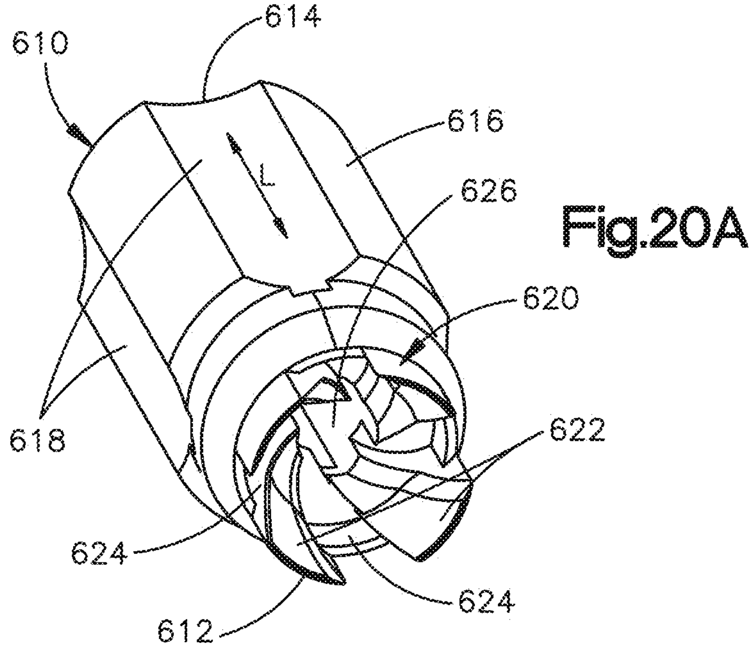
FIG. 20A is a perspective view of a shaping tool for removing excess cement for the mold assembly shown in FIG. 12.
Figure 20B:
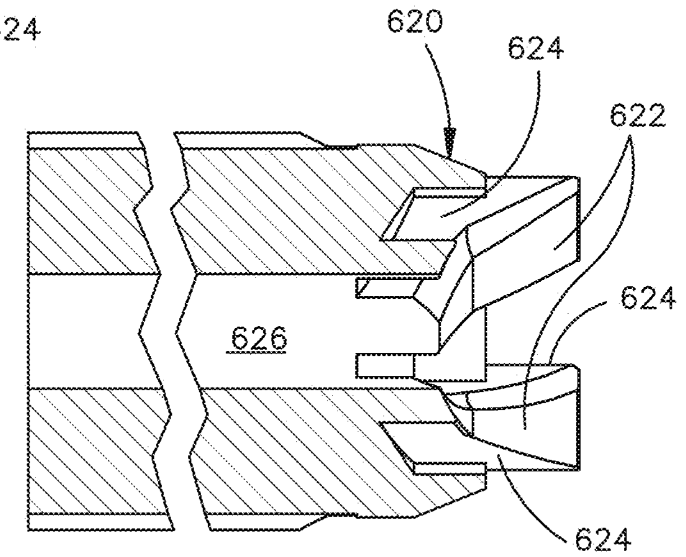
FIG. 20B is a cross-section side view of the shaping tool shown in FIG. 20A.
Figure 20C:
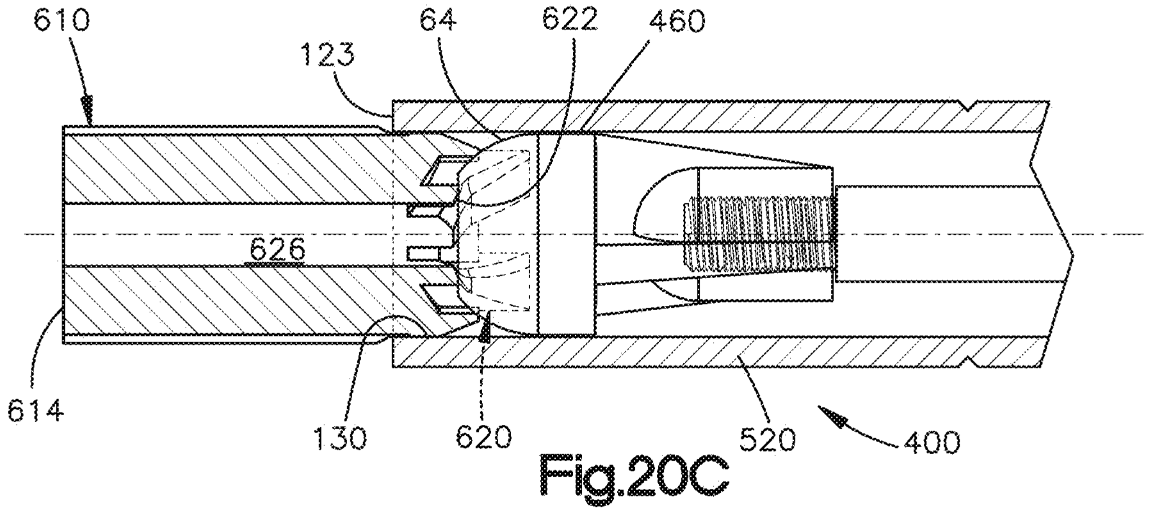
FIG. 20C is a partial cross-section side view of the shaping tool of FIG. 20A, illustrated engaged with the cap shown in FIG. 14A.

Referring now to FIGS. 20A-20C, the mold assembly 400 can include a shaping tool 610 for cleaning excess cement 85 from the distal end of the temporary spacer core 405. The shaping tool 610 has a proximal end 612, an opposed distal end 614 spaced from proximal end 612 along the longitudinal direction L, and a grip portion 616 that extends from the distal end 614 toward the proximal end 612. The grip portion 616 preferably defines grip features 618, such as recesses, knurls, and the like, to facilitate manipulation by the surgeon. The shaping tool 610 includes a cleaning formation 620 at the proximal end 612. As shown in FIG. 20C, the cleaning formation 620 is configured for insertion within the mold lumen 136 at the distal mold end 123 to engage the distal cap end 64. The cleaning formation 620 defines an engagement surface 622, which preferably has a concave geometry that is complimentary with the geometry of the distal end 64 of the cap 460. The cleaning formation 620 also defines a plurality of channels 624 for conveying the excess cement away from the cap 460. The channels 624 can extend along spiral-like paths and can be in fluid communication with a tool lumen 626 that extends from the cleaning formation 620 to the distal end 614. The channels 624 are preferably configured to receive and contain excess cement 85 dislodged from the cap 460, and preferably also to direct excess cement 85 inwardly into the tool lumen 626 for containment. It should be appreciated that although the channels 624 can direct some of the excess cement through the lumen 626 and out the distal end 614, such conveyance out the distal end 614 need not be necessary for the shaping tool 610 to sufficiently clean excess cement from the cap 460.

Figure 21:
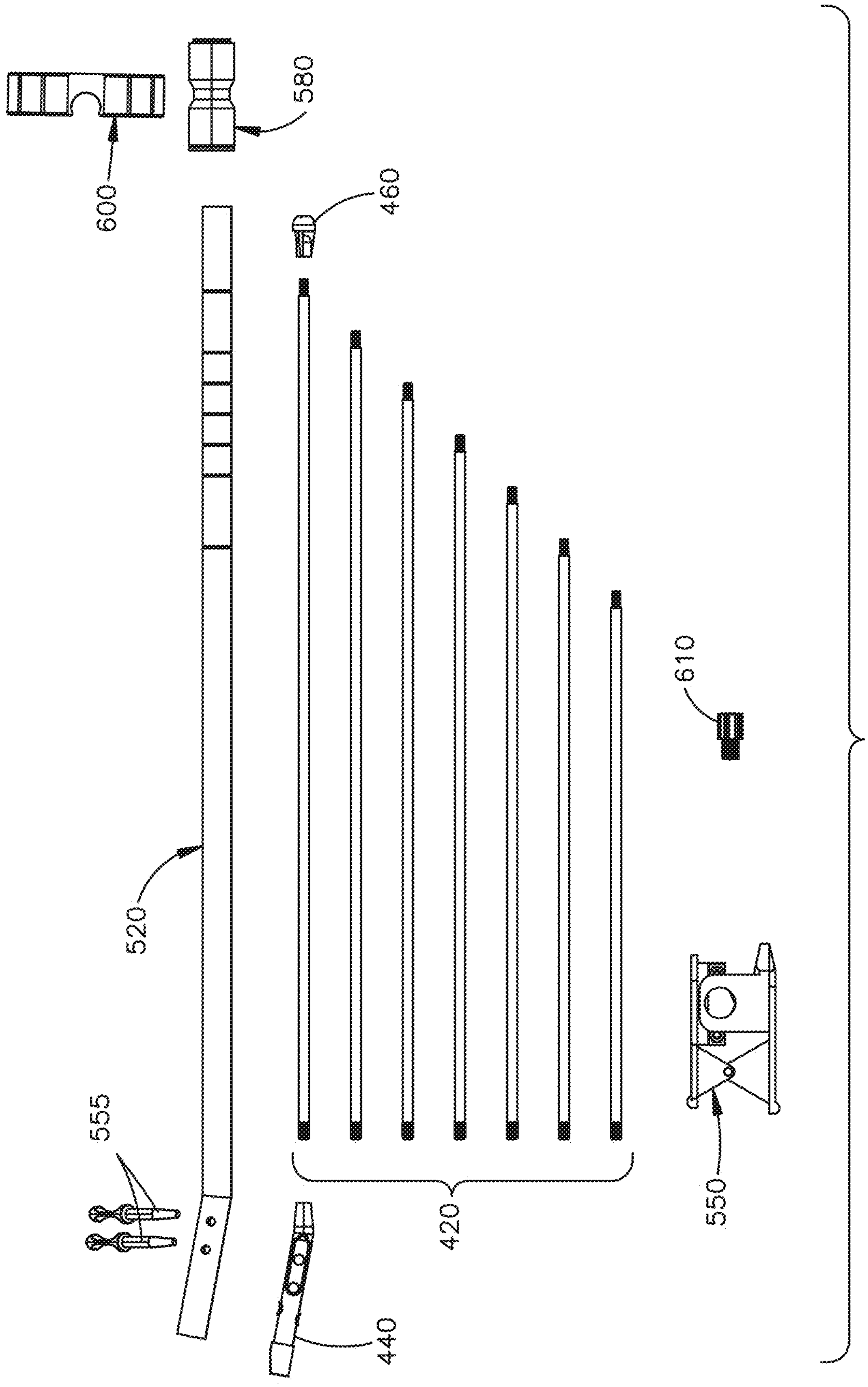
FIG. 21 is a plan view of a kit that includes the mold assembly shown in FIG. 12.

Referring now to FIG. 21, the mold assembly 400 can be provided in a kit 700 for forming the temporary cement spacer 1. The kit 700 of the present embodiment can include a mold body 520, at least one adapter 580, a locking component 440, at least one bore plug 555, at least one rod 420, and a cap 460. It should be appreciated that various combinations of the foregoing components can optionally be provided in the kit 700 already connected, as described above. In some embodiments of the kit 700, the at least one rod 420 can include a plurality of rods 420, such as, for example, two (2), three (3), four (4), five (5), six (6), seven (7), eight (8), nine (9), ten (10), or more than ten rods 420. In a preferred embodiment, each rod 420 of the plurality of rods 420 has a length that differs from those of each other rod 420. Thus, the kit 700 allows the surgeon or other medical professional to select the rod 420 having the desired rod length for use forming the temporary spacer 1 having a desired spacer length, thereby allowing the surgeon to customize the spacer core 405 based on patient-specific anatomy.

It should be appreciated that the kit 700 can be a single-use kit that contains an entire system for forming the temporary spacer 1. In such embodiments, the kit 700 can include a cement injection device 210, a cement mixing device, and one or more pre-packaged quantities of cement material. The single-use kit 700 of such embodiments can also include components for implanting the formed temporary spacer 1 in patient anatomy. For example, the kit 700 can include an insertion instrument 300 and accompanying insertion screw 303 for coupling to the proximal end of the locking component 440. The kit 700 can further include at least one locking bone screw, such as a plurality of locking screws, such as two (2), three (3), four (4), five (5), six (6), seven (7), eight (8), or more than eight locking screws that are configured to be disposed respectively in the locking bores 555 and secure the temporary spacer 1 to bone.

The kit 700 can be employed in a method of performing a surgical revision procedure, such as for removing and temporarily replacing an implant. The procedure can include a method of forming or otherwise constructing an antimicrobial-eluting temporary cement spacer 1. One example of such a method for constructing the temporary spacer includes a step of selecting a rod 420 having a desired length from the plurality of rods 420 in the kit 700, such as from a plurality of seven (7) rods 420 having respective lengths of 285 mm, 315 mm, 330 mm, 345 mm, 360 mm, 375 mm, and 405 mm, by way of non-limiting examples. The surgeon can assemble the spacer core 405 by coupling the proximal rod end 22 of the selected rod 420 to the locking component 440 and the distal rod end 24 to the cap 460, in the manners described above. The desired length mold body 520 can be determined, such as by placing the assembled spacer core 405 alongside the mold body 520, and identifying the marking 525 on the mold body 520 that aligns with the distal cap end 64. The surgeon can prepare the mold body 520 for cutting at the respective marking 525 by inserting the mold body 520 into the first pair of slots 562 of the cutter 550 so that the reference formation 566 aligns with the respective marking 525, after which the blade 558 can be employed to cut the mold body 520 at the marking 525. The cutter 550 can then be removed from the mold body 520.

The surgeon can subsequently begin assembling the mold, such as by inserting the assembled spacer core 405 through the proximal mold opening 131 and into the lumen 136. The surgeon can align the locking bores 55 of the locking component 440 with the associated mold bores 145 in the mold body 520 and insert one or more of the bore plugs 555 through the respective one or more mold bores 145 and respective one or more locking bores 55. It should be appreciated that each bore plug 555 can ensure the proper orientation of the spacer core 405 in the mold body 520 and can also prevent the spacer core 405 from moving relative to the mold body 520 responsive to the pressure generated while injecting the bone cement into the mold body 520. The adapter 580 can be coupled to the mold body 520. In particular, the distal mold end 123 can be inserted within the proximal adapter opening 191 until fully seated within the adapter lumen 186. At this stage, the mold can be characterized as being fully constructed, or at least substantially fully constructed. The constructed mold can be set aside while the bone cement is mixed and ready for injecting into the mold.

To facilitate cement injection, the injection tube 212 of the injection device 210 can be inserted within the distal adapter opening 193 until fully seated within the adapter lumen 186 and in fluid communication with the mold lumen 136. Preferably, as soon as the cement is mixed, the injection device 210 is employed to inject the mixed cement through the injection tube 212 and into the mold, specifically, through the distal cap opening 75 and along the channels 466 and into the annular space between the rod outer surface 26 and the inner mold surface 138, preferably at a constant rate. During injection, the surgeon preferably observes the cement advancing through the mold through the translucent mold body 520. Injection is continued so that the cement is forced along the main recessed surface portion 449 of the locking component 440 and around the one or more projections 49 thereof. Preferably, injection continues at least until the cement reaches the channel 447 at the proximal end of the locking component 440. If necessary, the proximal plug member 470 can be inserted within the proximal locking inner surface 51 to prevent the threads therein from contact with the cement.

After the mold is filled, the mold body 520 can be removed from the adapter 580, which can be facilitated by depressing the first release member 588 in the manner described above. Once removed, the adapter 580 and the injection device 210 can be discarded. After the adapter 580 is removed from the mold body 520, the shaping tool 610 employed to remove excess cement from the distal cap end 64. In particular, the cleaning formation 620 can be inserted within the mold lumen 136 so that the engagement surface 622 engages the distal cap end 64, as described above. The surgeon can rotate the shaping tool 610 about the central axis C to remove the excess cement. It should be appreciated that the cleaning step can be repeated several times as the cement cures, and may necessarily be repeated until the cement reaches a doughy state in the curing process. Preferably, the distal cap end 64 will be visible at the conclusion of the cleaning step. The fully assembled, injected mold can be set aside until the bone cement has fully cured.

Figure 22:
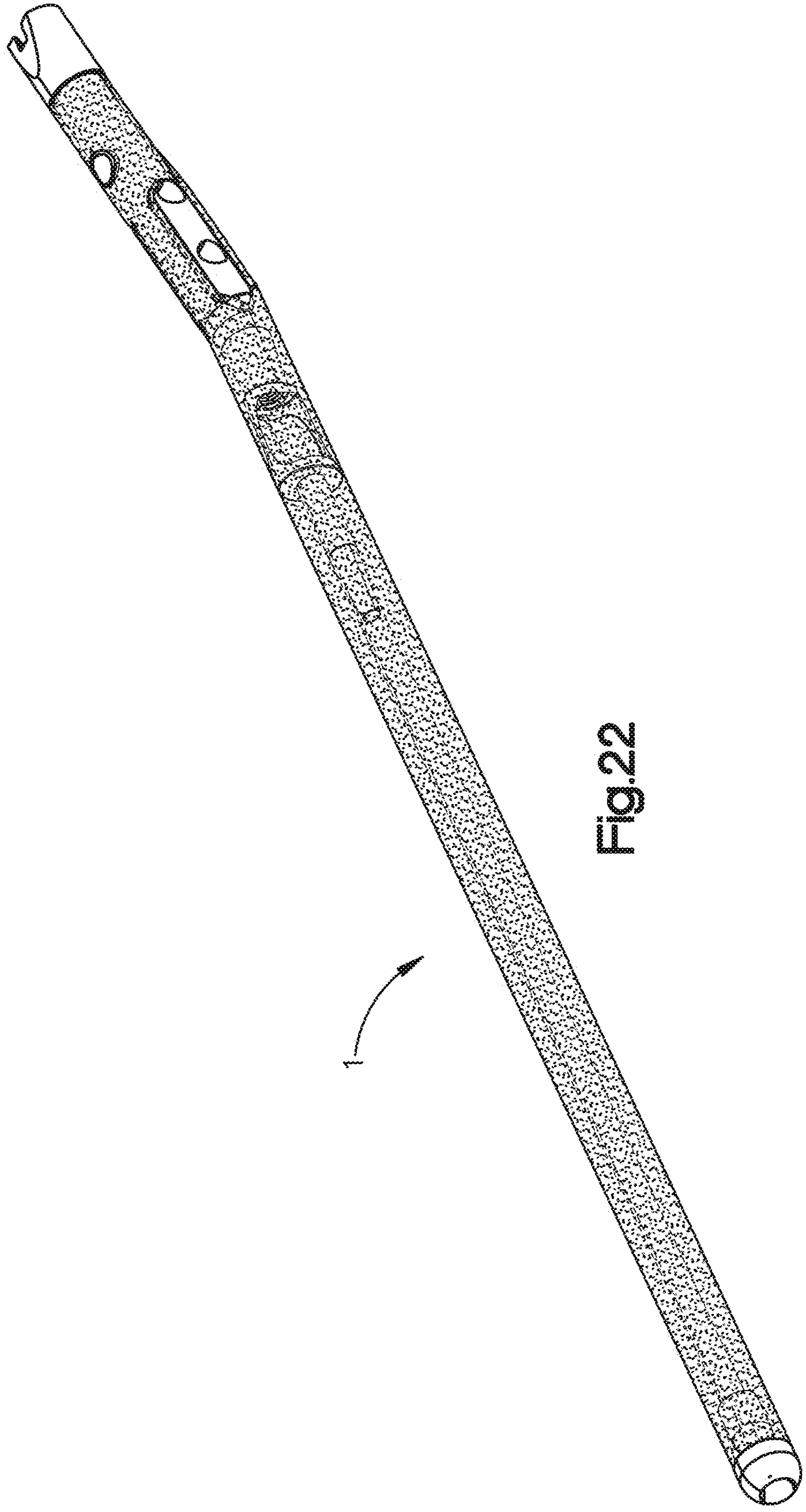
FIG. 22 is a perspective view of a temporary spacer constructed from the mold assembly and related components shown in FIGS. 12-21.

After the cement has cured, the surgeon can remove the one or more bore plugs 555 and the proximal plug member 470 in preparation for removing the mold body 520 from the spacer core 405. For removal, the mold body 520 can be inserted within the second pair of slots 564 of the cutter 550, and the blade 558 can be employed to cut a first longitudinal slit along the length of the mold body 520. After the first longitudinal slit is cut, the mold body 520 can be rotated about the central axis C relative to the cutter 550, such as by 180 degrees about the axis C, and a second longitudinal slit can be cut along the length of the mold body 520 in similar fashion. After the first and second full-length slits are cut, the surgeon can grip the opposite portions of the cut mold body and separate the mold body from the spacer core 405. The temporary spacer 1 formed according to the foregoing steps is shown in FIG. 22. The surgeon can then prepare the temporary spacer 1 for implantation, such as be coupling the temporary spacer 1 to an insertion instrument 300, as described above.

It should be appreciated that the various features of the temporary spacers 1, mold assemblies, and components thereof that are described above are provided as exemplary features of a surgical system. These features can be adjusted as needed without departing from the scope of the present disclosure.

It should further be appreciated when a numerical preposition (e.g., "first", "second", "third") is used herein with reference to an element, component, dimension, or a feature thereof (e.g., "first" member, "second" member, etc.), such numerical preposition is used to distinguish said element, component, dimension, and/or feature from another such element, component, dimension and/or feature, and is not to be limited to the specific numerical preposition used in that instance. For example, a "first" member can also be referred to as a "second" member in a different context without departing from the scope of the present disclosure, so long as said members remain properly distinguished in the context in which the numerical prepositions are used.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. In particular, one or more of the features from the foregoing embodiments can be employed in other embodiments herein. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A mold assembly for forming a temporary cement spacer, comprising:

a spacer core comprising:

a rod defining a central axis of the mold assembly and having a proximal rod end and a distal rod end opposite the proximal rod end along the central axis, the rod further defining an outer rod surface extending between the proximal rod end and the distal rod end;

a locking component defining a distal locking end and a proximal locking end opposite the distal locking end along the central axis, the distal locking end attached to the rod at the proximal rod end, the locking component further defining at least one locking bore extending through the locking component in a radial direction with respect to the central axis, the at least one locking bore configured to receive a locking screw; and, a mold body extending along the central axis, the mold body defining a proximal mold end and a distal mold end opposite the proximal mold end along the central axis, the proximal mold end including a proximal mold opening and the distal mold end including a distal mold opening, wherein the mold body defines an inner mold surface extending between the proximal mold opening and the distal mold opening, the inner mold surface defines a mold lumen, and the spacer core is disposed within the mold lumen such that the locking component is disposed within the mold lumen at the proximal mold end;

at least one bore plug disposed in the at least one locking bore; and, an adapter configured to operably couple to the mold body at the distal mold end, the adapter configured to operably couple the mold body to a bone cement injection device so as to provide a fluid pathway from the bone cement injection device through the distal mold opening to the mold lumen.

2. The mold assembly of claim 1, wherein the mold body further comprises at least one mold bore, the at least one mold bore extends through the mold body and the mold lumen in a radial direction with respect to the central axis, and wherein the at least one bore plug is configured to be disposed in the at least one mold bore.

3. The mold assembly of claim 2, wherein the at least one mold bore is aligned with the at least one locking bore, and the at least one bore plug is disposed within both the at least one locking bore and the at least one mold bore.

4. The mold assembly of claim 1, further comprising a cutting device having a blade configured to cut the mold body to a desired length as measured along a longitudinal direction, wherein the central axis is oriented along the longitudinal direction, and the radial direction is perpendicular to the longitudinal direction.

5. The mold assembly of claim 4, wherein the cutting device has a first mounting formation configured to receive the mold body and retain the mold body relative to the blade, such that the blade is oriented along a transverse direction that is perpendicular to the longitudinal direction.

6. The mold assembly of claim 5, wherein the cutting device further has a second mounting formation configured to receive the mold body and retain the mold body relative to the blade, such that the blade is oriented along the longitudinal direction, wherein the blade is configured to slice the mold body longitudinally from the proximal mold end to the distal mold end.

7. A kit for forming a temporary cement spacer, comprising:

at least one rod defining a proximal rod end and a distal rod end opposite the proximal rod end;

a locking component configured to operably couple to the rod, the locking component defining a distal locking end and a proximal locking end opposite the distal locking end, the distal locking end configured to attach to the rod at the proximal rod end, the locking component further defining at least one locking bore extending through the locking component and configured to receive a locking screw, wherein the at least one rod and the locking component are configured to form a spacer core when operably coupled;

at least one bore plug configured to be removably disposed within the at least one locking bore;

a mold body defining a proximal mold end and a distal mold end opposite the proximal mold end and an outer mold surface extending from the proximal mold end and the distal mold end, the mold body further defining a proximal mold opening at the proximal mold end and a distal mold opening at the distal mold end and an inner mold surface extending between the proximal mold opening and distal mold opening, the inner mold surface defining a mold lumen extending therebetween, wherein the spacer core is configured to be disposed in the mold lumen;

an adapter configured to operably couple to the mold body at the distal mold end, wherein the adapter is further configured to couple a bone cement injection device to the distal mold opening so as to provide a fluid pathway from the cement injection device to the mold lumen; and, a cap configured to operably couple to the distal rod end.

8. The kit of claim 7, wherein the at least one rod comprises a plurality of rods, wherein each rod of the plurality of rods has a length measured between the proximal rod end and the distal rod end, and wherein each rod length is different than any other rod length of the plurality of rods.

9. The kit of claim 7, further comprising an insertion instrument, the insertion instrument configured to operably couple to the proximal end of the locking component, wherein the insertion instrument is configured for implanting the temporary spacer.

10. The kit of claim 7, further comprising a tool having a proximal tool surface that has a complementary geometry to a distal surface of the cap, the tool defining a plurality of channels recessed from the proximal surface, wherein the tool is configured so as to engage the distal cap surface with the proximal tool surface in a manner removing excess cement from the cap, wherein the plurality of channels are configured to direct at least some of the excess cement away from the cap.

11. A method of preparing an antimicrobial-eluting temporary cement spacer, the method comprising:

inserting a spacer core into a lumen of a mold body, the spacer core including a rod and a locking component connected to the rod, wherein the locking component includes at least one locking bore;

coupling a bone cement injection device to the mold body via an adapter to provide a fluid pathway from the bone cement injection device into the lumen of the mold body;

disposing at least one bore plug into the at least one locking bore;

injecting bone cement material including one or more antimicrobial agents into the lumen of the mold body through the fluid pathway and along at least a portion of an outer surface of the rod;

curing the bone cement material on the outer surface of the rod so as to form a cement coating on the spacer core, thereby forming the antimicrobial eluting temporary cement spacer;

decoupling the bone cement injection device from the mold body;

removing the at least one bore plug from the at least one locking bore; and, separating the mold body from the antimicrobial eluting temporary cement spacer.

12. The method of claim 11, further comprising, prior to the step of inserting the spacer core into the mold lumen, connecting the rod to the locking component, wherein the connecting step comprises operably coupling a proximal end of the rod to a distal end of the locking component.

13. The method of claim 11, wherein the mold body defines a mold length measured from a proximal mold end to an opposing distal mold end, the method comprising removing a portion of the mold body length from either the proximal mold end or the distal mold end.

14. The method of claim 11, wherein the mold body defines an outer surface of the mold extending from the proximal mold end to the distal mold end, and wherein the mold body includes at least one mold bore extending from the outer mold surface through the mold lumen, the method comprising aligning the at least one locking bore with the at least one mold bore, and the step of disposing the at least one bore plug into the at least one locking bore further comprises disposing the at least one bore plug in the at least one mold bore.

15. The method of claim 11, further comprising attaching a cap to the rod, wherein the cap defines a proximal cap end and an opposing distal cap end, wherein the proximal cap end is operably coupled to a distal end of the rod, wherein the step of injecting bone cement material includes forcing the bone cement material through a plurality of channels extending through the cap from the distal cap end toward the proximal cap end.

16. The method of claim 15, wherein the step of injecting bone cement material includes forcing the bone cement material through a distal cap opening, through the plurality of channels, and into the mold lumen.

* * * * *